US012779099B2

(12) United States Patent
Myrick et al.

(10) Patent No.: US 12,779,099 B2
(45) Date of Patent: Nov. 3, 2026

(54) SYSTEMS AND METHODS FOR COMBINED VESSEL OCCLUSION AND GAS ENRICHMENT THERAPY

(71) Applicant: Zoll Circulation, Inc., San Jose, CA (US)

(72) Inventors: Stephen Elwood Myrick, Tustin, CA (US); Jeffrey Lance Creech, Los Angeles, CA (US); Gary A. Freeman, Waltham, MA (US)

(73) Assignee: Zoll Circulation, Inc., San Jose, CA (US)

( * ) Notice: Subject to any disclaimer, the term of this patent is extended or adjusted under 35 U.S.C. 154(b) by 1255 days.

(21) Appl. No.: 17/707,464

(22) Filed: Mar. 29, 2022

(65) Prior Publication Data

US 2022/0313885 A1 Oct. 6, 2022

Related U.S. Application Data

(60) Provisional application No. 63/168,169, filed on Mar. 30, 2021.

(51) Int. Cl.
*A61M 1/36* (2006.01)
*A61B 5/0215* (2006.01)
*A61M 25/00* (2006.01)

(52) U.S. Cl.
CPC ......... *A61M 1/3613* (2014.02); *A61B 5/0215* (2013.01); *A61M 1/3621* (2013.01); *A61M 25/0029* (2013.01); *A61M 2202/0476* (2013.01)

(58) Field of Classification Search
CPC ........ A61M 1/32; A61M 1/3613; A61M 1/36; A61M 1/3621; A61M 2202/0476;
(Continued)

(56) References Cited

U.S. PATENT DOCUMENTS 5,599,296 A * 2/1997 Spears .................... B01F 23/29 604/24
5,788,647 A * 8/1998 Eggers ................. A61B 5/1459 600/479
6,582,387 B2 6/2003 Derek et al.
6,743,196 B2 6/2004 Barbut et al.
(Continued)

FOREIGN PATENT DOCUMENTS

WO WO 2021/202603 10/2021

OTHER PUBLICATIONS

EP Extended European Search Report in European Appln. No. 22782007.3, mailed on Jan. 21, 2025, 8 pages.
(Continued)

*Primary Examiner* — Jason E Flick
(74) *Attorney, Agent, or Firm* — Fish & Richardson P.C.

(57) ABSTRACT

A system delivers gas-enriched blood or liquid within the vasculature of a patient while partially obstructing a flow of blood within the vasculature of the patient. The system may include a first catheter configured for inserting into a vasculature of a patient to deliver gas-enriched blood or liquid to a region of the vasculature of the patient. The system may include a second catheter configured for inserting into the vasculature of the patient. The second catheter includes lumens and an occlusion structure configured to partially obstruct a flow of blood within the vasculature of the patient while allowing the first catheter to deliver the gas-enriched blood or liquid to the region of the vasculature, and to divert the blood flow to the region where the gas-enriched blood or liquid is delivered.

19 Claims, 14 Drawing Sheets

(58) Field of Classification Search

CPC .......... A61M 25/0029; A61M 25/0026; A61M 2025/1052; A61M 2230/205; A61M 2230/20; A61M 2230/202; A61M 2230/30; A61M 2230/50; A61M 1/3659; A61M 1/3666; A61M 1/36224; A61M 1/1698; A61M 25/003; A61M 2025/0031; A61M 2230/005; A61M 25/0082; A61M 2025/0085; A61M 2025/0087; A61M 2025/0086; A61B 5/021; A61B 5/02; A61B 5/0215; A61B 5/02158

See application file for complete search history.

(56) References Cited

U.S. PATENT DOCUMENTS

| | | | | | |
|---|---|---|---|---|---|
| 7,820,102 | B2 | 10/2010 | Myrick et al. | | |
| 8,192,384 | B2 | 6/2012 | Myrick et al. | | |
| 8,246,564 | B2 | 8/2012 | Myrick et al. | | |
| 9,919,276 | B2 * | 3/2018 | Myrick | A61M 1/32 | |
| 10,335,152 | B2 | 7/2019 | Barbut et al. | | |
| 10,773,009 | B2 | 9/2020 | Pile-Spellman et al. | | |
| 2011/0196282 | A1 * | 8/2011 | Kassab | A61M 1/3659 | 604/9 |
| 2012/0172781 | A1 * | 7/2012 | Wang | A61M 1/3613 | 604/509 |

OTHER PUBLICATIONS

PCT International Search Report and Written Opinion in International Appln. No. PCT/US2022/022308, dated Jun. 23, 2022, 14 pages.

* cited by examiner

SYSTEMS AND METHODS FOR COMBINED VESSEL OCCLUSION AND GAS ENRICHMENT THERAPY

CLAIM OF PRIORITY

This application claims priority under 35 U.S.C. § 119(e) to U.S. Provisional Application Ser. No. 63/168,169, filed on Mar. 30, 2021, the entire contents of which are hereby incorporated by reference.

TECHNICAL FIELD

The disclosure relates to catheters and systems for the delivery of gas-enriched liquid into a patient.

BACKGROUND

Gas-enriched liquids are desirable in a wide variety of applications. However, at ambient pressure, the relatively low solubility of many gases, such as oxygen or nitrogen, within a liquid, such as water, produces a relatively low concentration of the dissolved gas in the liquid. One method of obtaining an increase in the gas concentration level without significant increase in liquid volume involves an injection and mixing of a gas-enriched liquid into a liquid of interest. A liquid can be gas enriched at high pressure.

Conventional methods for the delivery of oxygenated blood or oxygen-enriched liquids to tissues and bodily liquids involve the use of extracorporeal circuits for blood oxygenation. Extracorporeal circuits require withdrawing blood from a patient, circulating the blood through an oxygenator to increase blood oxygen concentration, and then delivering the blood back to the patient.

SUMMARY

In an aspect, a catheter is provided that is insertable into a vasculature of a patient. The catheter is configured for delivering gas-enriched blood within the vasculature of a patient while at least partially obstructing a flow of blood within the vasculature of the patient. The catheter is configured to be connected to a gas-enrichment chamber to receive gas-enriched blood. The gas-enrichment chamber may be configured to mix the blood of the patient with a gas-enriched liquid to provide the gas-enriched blood. The catheter may comprise a first catheter configured to be inserted into a vasculature of a patient and deliver gas-enriched blood to a region of the vasculature of the patient. The catheter includes one or more lumens configured to receive the gas-enriched blood from the gas-enrichment chamber. In some implementations, the catheter may include one or more occlusion structures configured to at least partially obstruct a flow of blood within the vasculature of the patient while allowing delivery of the gas-enriched blood to the region of the vasculature. The one or more occlusion structures of the catheter may divert the blood flow to the region where the gas-enriched blood is delivered. In some implementations, a second catheter is inserted into the vasculature of the patient. The second catheter may be separate from the first catheter. The second catheter may include the one or more occlusion structures configured to at least partially obstruct the flow of blood within the vasculature of the patient while allowing delivery of the gas-enriched blood via the first catheter to the region of the vasculature. The one or more occlusion structures of the second catheter may be configured to divert the blood flow to the region where the gas-enriched blood is delivered by the first catheter. In some implementations, the gas-enriched blood is a supersaturated oxygen enriched blood. In some implementations, one or more sensors are configured to measure one or more parameters of blood of the patient, such as blood pressure, partial pressure of oxygen ($pO_2$) in the blood, saturation of oxygen ($SO_2$) in the blood, or blood flow rate. The measured parameters may be used for controlling operation of the first catheter, the second catheter, or both the first catheter and the second catheter.

In another aspect, there is provided a system for delivering gas-enriched blood within the vasculature of a patient while at least partially obstructing a flow of blood within the vasculature of the patient. The system may include a gas-enrichment chamber that is configured to mix the blood of the patient with a gas-enriched liquid. The system includes a first catheter coupled to the gas-enrichment chamber. The first catheter may be configured to be inserted into a vasculature of a patient and deliver gas-enriched blood to a region of the vasculature of the patient. The first catheter comprises one or more lumens configured to receive the gas-enriched blood from the gas-enrichment chamber. The system further includes a second catheter. The second catheter may be configured to be inserted into the vasculature of the patient. The second catheter may comprise one or more lumens and may comprise one or more occlusion structures configured to at least partially obstruct a flow of blood within the vasculature of the patient. The first and second catheters may be arranged such that, the one or more occlusion structures of the second catheter at least partially obstructs the flow of blood within the vasculature of the patient while allowing the first catheter to deliver the gas-enriched blood to the region of the vasculature, and divert the blood flow to the region where the gas-enriched liquid is delivered. The system may comprise one or more sensors. The one or more sensors may be configured to measure one or more parameters of blood of the patient. For example, the one or more sensors may be configured to measure one or more parameters of blood of the patient for providing feedback to control the first and/or second catheters. The system may be configured to provide a visual and/or audible alert for a user based on the measured one or more parameters. The system may be configured to control operation of the first catheter, the second catheter, or both the first catheter and the second catheter based on the measured one or more parameters. "At least partially obstructing" encompasses "partially obstructing" and "entirely obstructing". Implementations of the above aspects can include one or more of the following features.

In some implementations, the system includes an introducer sheath through which at least the first catheter can be inserted into the vasculature. The introducer sheath may have a blood port through which blood may be withdrawn from the patient. The system may be arranged so that the withdrawn blood flows to the gas enrichment chamber where it is enriched with gas, the gas-enriched blood then flowing to the patient through the first catheter. The system, the introducer sheath or the first or second catheter may comprise a blood withdraw lumen for withdrawn blood from the patient. The blood withdraw lumen may be arranged to withdraw blood upstream from the one or more occlusion structures. The one or more occlusion structures may be arranged to be upstream from the region of the vasculature of the patient in which the one or more lumens of the first catheter are configured to deliver gas-enriched blood.

In some implementations, the one or more occlusion structures is configured to at least partially obstruct the flow of blood within the vasculature. In some implementations, a catheter length is between 50-100 centimeters. In some implementations, a sheath size is 7, 10, or 12 French. In some implementations, the guide wire diameter is between 0.033 and 0.040 inches. In some implementations, the occlusion structure diameter (e.g., a balloon) is between 5-30 millimeters, e.g., inflatable between 5-30 millimeters. In some implementations, occlusion structure diameter is between 9-26 millimeters. In some implementations, occlusion structure diameter is between 10-50 millimeters. In some implementations, the occlusion structure volume (e.g., for a balloon) is between 3-60 milliliters. In some implementations, the occlusion structure volume (e.g., for a balloon) is about 25-30 milliliters. In some implementations, the catheter and/or one or more uninflated balloons can have an outside diameter of about 0.050 to 0.200 inches, e.g., 0.095 inches (7.24 French). In some implementations, these various ranges of sizes and volumes of the catheter and/or occlusion structures may partially obstruct the flow of blood within the vasculature by producing a vessel occlusion ranging from 20%-80%, depending on the catheter and/or occlusion structure dimensions.

In some implementations, the first catheter is configured to withdraw blood from the patient and to deliver the blood to the gas-enrichment chamber.

In some implementations, the system includes a cannula, the cannula configured to withdraw blood from the patient and deliver the blood to the gas-enrichment chamber.

In some implementations, the one or more sensors comprises a blood pressure sensor, $pO_2$ sensor, $SO_2$ sensor or flow rate sensor. The one or more sensors may be provided on the first or second catheter. The one or more sensors may be provided upstream or downstream of the one or more occlusion structures.

In some implementations, the system includes a control system. The control system may be configured to control operation of the first catheter, the second catheter, or both the first catheter and the second catheter. The control system may be configured to control operation of the first catheter, the second catheter, or both the first catheter and the second catheter based on one or more signals representing the measured one or more parameters. Controlling operation of the first catheter may include controlling a concentration of gas in the gas-enriched liquid. Controlling operation of the second catheter may include controlling an amount of occlusion caused by the one or more occlusion structures of the second catheter.

In some implementations, the control system is configured to: receive the one or more signals representative of the measured one or more parameters from the one more sensors. The control system may be configured to, based on the one or more signals: adjust an (amount of) occlusion caused by the one or more occlusion structures of the second catheter; adjust a concentration of gas in the gas-enriched liquid; or adjust both the occlusion and the concentration. The control system may adjust an occlusion percentage caused by the one or more occlusion structures of the second catheter.

In some implementations, the one or more parameters include blood pressure in the patient. The control system may be configured to, based on the one or more signals, adjust an occlusion caused by the one or more occlusion structures of the second catheter. In some implementations, adjusting the occlusion caused by the one or more occlusion structures comprises: increasing the occlusion in an initial control phase; and gradually reducing occlusion in a subsequent control phase until the blood pressure is within a target range.

In some implementations, the one or more sensors comprises a pressure measuring device operable to measure blood pressure in the vasculature upstream of the one or more occlusion structures. The pressure measuring device may be provided in the vasculature upstream of the one or more occlusion structures.

In some implementations, the pressure measuring device is a pressure tube inserted through a communicating lumen in the first or second catheter. The communicating lumen may be in fluid communication with the vasculature of the patient. The pressure tube may be proximally connected to a pressure monitor.

In some implementations, the pressure measuring device is a manometer mounted at the distal end of the second catheter.

In some implementations, the one or more parameters include $pO_2$ in the blood of the patient. The control system may be configured to, based on the one or more signals of the measured $pO_2$, adjust a concentration of oxygen in the gas-enriched liquid.

In some implementations, adjusting the concentration of oxygen in the gas-enriched liquid comprises: increasing the concentration of oxygen in an initial control phase; and gradually reducing concentration of oxygen in a subsequent control phase until the $pO_2$ is within a $pO_2$ target range.

In some implementations, adjusting both the occlusion and the concentration of oxygen based the one or more signals representing one or more parameters comprises: determining a target blood pressure and a target $pO_2$ in blood; causing, by the one or more occlusion structures, the blood pressure to be within a threshold range of the target blood pressure; and adjusting the concentration of oxygen in the gas-enriched liquid until the $pO_2$ is within a threshold range of the target $pO_2$.

The one or more occlusion structures may be one or more variable occlusion structures. The one or more lumens of the second catheter may be couple to the one or more occlusion structures to enable fluid communication to inflate or deflate the one or more occlusion structures. The one or more occlusion structures may be controllable so that the extent, or amount, of occlusion provided by the one or more occlusion structures may be varied. In some implementations, controlling or adjusting the occlusion caused by the one or more occlusion structures comprises oscillating a size of the one or more occlusion structures. Controlling or adjusting the occlusion caused by the one or more occlusion structures may comprise oscillating a size of the occlusion structure to prevent blood stasis.

In some implementations, controlling or adjusting the one or more occlusions caused by the occlusion structure comprises oscillating a size of the one or more occlusion structures to prevent cytokine buildup at or near the one or more occlusion structures.

In some implementations, the one or more parameters comprise cerebral oxygenation. The control system may be configured to cause an adjustment of an oxygen concentration in the gas-enriched liquid until the cerebral oxygenation measured by cerebral oximeter is within a threshold range of a target cerebral oxygenation level.

In some implementations, an adjustment of the oxygen concentration comprises an oxygen titration in the gas-enrichment chamber, which is in fluid communication with the first catheter.

In some implementations, the system includes a pump configured to draw blood of the patient into the gas-enrichment chamber; a first arterial line connecting an input of the gas-enrichment chamber to the blood port of the sheath; and a second arterial line connecting an outlet of the gas-enrichment chamber to the one or more lumens of the first catheter.

In some implementations, the one or more parameters comprise one or more of a blood pressure, $pO_2$, $SO_2$, and a flow rate of the blood of the patient. In some implementations, an IR sensor is used to measure $SO_2$ in the blood of the patient. In some implementations, the gas-enriched liquid comprises a supersaturated oxygen liquid. In some implementations, the supersaturated oxygen liquid has an $O_2$ concentration of 0.1-6 ml $O_2$/ml liquid (STP).

The one or more variable occlusion structures may be provided by one or more balloons. In some implementations, the one or more occlusion structures comprises one or more inflatable balloons, the balloons sized and configured to at least partially obstruct blood flow through an aorta (when inflated).

In some implementations, the one or more lumens of the second catheter comprise an inflation lumen configured to deliver fluid into at least one of the one or more inflatable balloons. The one or more lumens of the second catheter comprise a lumen in fluid communication with the vasculature of the patient.

In some implementations, the one or more occlusion structures comprises a cuff around a lumen structure of the second catheter.

In some implementations, the first and/or second catheter comprises a communicating lumen configured to provide fluid communication with the vasculature of the patient and through which arterial blood pressure can be measured.

In some implementations, the second catheter comprises a communicating lumen configured to receive the first catheter when the second catheter is in the vasculature of the patient. The first catheter may be configured to be advanced through the communicating lumen of the second catheter and into the vasculature of the patient.

In some implementations, the first catheter and the second catheter form a single, hybrid catheter. The first catheter and the second catheter may be provided by a single catheter.

In some implementations, the control system comprises: a first controller configured to control the operation of the first catheter; and a second controller configured to control the operation of the second catheter. The first controller may be separate from the second controller.

In some implementations, the gas-enriched blood comprises a supersaturated oxygen enriched blood. In some implementations, the supersaturated oxygen enriched blood has a $pO_2$ of 600-1500 mmHg (80-200 kPa).

In some implementations, the one or more occlusion structures is configured to produce a partially obstructed blood flow having a blood flow rate that is 20-80% of a non-occluded blood flow rate.

In an aspect, a catheter configured to be inserted into a vasculature of a patient, the catheter comprising: a catheter body, a connector configured for connecting the catheter body to a gas-enrichment chamber or gas-enriched liquid source. The gas-enrichment chamber may be configured to mix blood of the patient with a gas-enriched liquid to form a gas enriched blood. A lumen extends through the catheter body. The lumen is configured to receive the gas-enriched blood from the gas enrichment chamber, or gas-enriched liquid from the gas-enriched liquid source, and deliver the gas-enriched blood or liquid to a region of the vasculature of the patient. The catheter comprises one or more occlusion structures coupled to the catheter body. The one or more occlusion structures may be configured to at least partially obstruct a flow of blood within the vasculature of the patient while allowing the lumen to deliver the gas-enriched blood or liquid to the region of the vasculature and to divert the blood flow to the region where the gas-enriched blood is delivered. The catheter of this aspect may be provided with any of the features of the implementations described with respect to a preceding aspect.

In some implementations, the one or more occlusion structures are configured to partially obstruct the flow of blood within the vasculature by producing a vessel occlusion of 20-80%. In some implementations, the one or more occlusion structures is configured to produce a partially obstructed blood flow having a blood flow rate that is 20-80% of a non-occluded blood flow rate. In some implementation, the catheter and/or one or more occlusion structures may have dimensions similar to those described herein for a catheter having occlusion structures or balloons. In some implementations, the one or more occlusion structures is an inflatable balloon; and the catheter body comprises a second lumen configured to deliver fluid into the inflatable balloon. In some implementations, catheter body further comprises a communicating lumen in fluid communication with the vasculature of the patient and through which arterial blood pressure can be measured. In some implementations, an arterial line measures pressure via the communicating lumen.

In some implementations, the system includes a pressure tube carried by the catheter and proximally connected to a pressure monitor for measuring arterial blood pressure of the patient. In some implementations, the gas-enriched blood is formed in the gas-enrichment chamber by mixing blood withdrawn from the patient with a gas-enriched liquid.

In some implementations, the gas-enriched liquid comprises a supersaturated oxygen liquid. In some implementations, the supersaturated oxygen liquid has an $O_2$ concentration of 0.1-6 ml $O_2$/ml liquid (STP).

In some implementations, the gas-enriched blood comprises a supersaturated oxygen enriched blood. In some implementations, the supersaturated oxygen enriched blood comprises a supersaturated oxygen enriched blood having a $pO_2$ of 600-1500 mmHg (80-200 kPa).

In an aspect, there is provided a system for delivering gas-enriched liquid within the vasculature of a patient while at least partially obstructing a flow of blood within the vasculature of the patient. The system comprises a source of a gas-enriched liquid. The system comprises a first catheter configured to be coupled to the source of the gas-enriched liquid. The first catheter may be configured to be inserted into a vasculature of a patient and may be configured to deliver the gas-enriched liquid to a region of the vasculature of the patient. The first catheter may comprise one or more lumens. The one or more lumens may be configured to receive the gas-enriched liquid from the source of the gas-enriched liquid. The system may comprise a second catheter. The second catheter may be configured to be inserted into the vasculature of the patient, the second catheter may comprise one or more lumens and may comprise an occlusion structure. The occlusion structure may be configured to at least partially obstruct a flow of blood within the vasculature of the patient while allowing the first catheter to deliver the gas-enriched liquid to the region of the vasculature, and may be configured to divert the blood flow to the region where the gas-enriched liquid is delivered. In some implementations, the first catheter comprises two or more capillaries extending from a tip of the first catheter, the two or more capillaries configured to simultaneously dispense respective streams of the gas enriched liquid directly into the vasculature of the patient.

In one or more implementations, the first catheter is configured to position the two or more capillaries at one or more predetermined angles relative to one another, such that the streams of the gas enriched liquid intersect and mix with the patient's blood.

In one or more implementations, the system further comprises a controller and one or more sensors, wherein the one or more sensors are configured to measure one or more parameters of blood of the patient. Operation of the first catheter, the second catheter, or both the first catheter and the second catheter may be controlled based on the measured one or more parameters.

In one or more implementations, the controller is configured for receiving, from one or more sensors, a signal representing a measured blood pressure in the vasculature of the patient and based on the measured blood pressure, adjusting an occlusion percentage in the vasculature of the patient caused by an occlusion structure of the catheter.

In one or more implementations, the controller is configured for receiving, from one or more sensors, a signal representing a measured $pO_2$ in the vasculature of the patient. Based on the measured $pO_2$, the controller may adjust a concentration of oxygen in the gas-enriched liquid. The controller may be configured to deliver the gas-enriched liquid having the adjusted concentration of oxygen to the region of the vasculature of the patient.

In one or more implementations, the controller is configured for adjusting both the concentration of gas in a gas-enriched liquid and the occlusion percentage in the vasculature of the patient.

In one or more implementations, the source of gas-enriched liquid comprises gas-enrichment chamber configured to form the gas-enriched liquid by mixing gas with atomized liquid.

In one or more implementations, the gas-enriched liquid comprises a supersaturated oxygen liquid.

In one or more implementations, the supersaturated oxygen liquid has an $O_2$ concentration of 0.1-6 ml $O_2$/ml liquid (STP).

In an aspect, a catheter is configured to be inserted into a vasculature of a patient, the catheter comprising: a catheter body; a connector configured for connecting the catheter body to a source of a gas-enriched liquid; a lumen extending through the catheter body, the lumen configured to receive the gas-enriched liquid from the source of a gas-enriched liquid and deliver the gas-enriched liquid to a region of the vasculature of the patient; and an occlusion structure coupled to the catheter body. The occlusion structure may be configured to partially obstruct a flow of blood within the vasculature of the patient while allowing the lumen to deliver the gas-enriched liquid to the region of the vasculature and to divert the blood flow to the region where the gas-enriched liquid is delivered.

In one or more implementations, the first catheter comprises two or more capillaries extending from a tip of the first catheter, the two or more capillaries configured to simultaneously dispense respective streams of the gas enriched liquid directly into the vasculature of the patient.

In one or more implementations, the first catheter is configured to position the two or more capillaries at one or more predetermined angles relative to one another, such that the streams of the gas enriched liquid intersect and mix with the patient's blood.

In one or more implementations, one or more sensors are configured to measure one or more parameters of blood of the patient. Operation of the first catheter, the second catheter, or both the first catheter and the second catheter may be controlled based on the measured one or more parameters.

In one or more implementations, a controller is configured for receiving, from one or more sensors, a signal representing a measured blood pressure in the vasculature of the patient. Based on the measured blood pressure, the controller may adjust an occlusion percentage in the vasculature of the patient caused by an occlusion structure of the catheter.

In one or more implementations, a controller is configured for receiving, from one or more sensors, a signal representing a measured $pO_2$ in the vasculature of the patient. Based on the measured $pO_2$, the controller may adjust a concentration of oxygen in the gas-enriched liquid. The controller may be configured to deliver the gas-enriched liquid having the adjusted concentration of oxygen to the region of the vasculature of the patient.

In one or more implementations, a controller is configured for adjusting both the concentration of gas in a gas-enriched liquid and the occlusion percentage in the vasculature of the patient.

In one or more implementations, the gas-enriched liquid comprises a supersaturated oxygen liquid.

In one or more implementations, the supersaturated oxygen liquid has an $O_2$ concentration of 0.1-6 ml $O_2$/ml liquid (STP).

In a general aspect, a method of treating a patient comprises inserting a first catheter into a vasculature of the patient, the first catheter comprising one or more occlusion structures configured to at least partially obstruct a flow of blood within the vasculature of the patient; inserting a second catheter into the vasculature of a patient, the second catheter comprising one or more lumens configured to receive gas-enriched liquid from a gas-enrichment chamber; delivering the gas-enriched liquid to a region of the vasculature of the patient through the one or more lumens of the second catheter; and controlling the one or more occlusion structures of the first catheter to at least partially obstruct the flow of blood within the vasculature of the patient, wherein the first catheter at least partially obstructs the flow of blood within the vasculature of the patient while allowing the second catheter to deliver the gas-enriched liquid to the region of the vasculature of the patient, and diverts the blood flow to the region where the gas-enriched liquid is delivered.

In some implementations, the one or more occlusion structures partially obstructs the flow of blood within the vasculature by producing a vessel occlusion of 20-80%. In some implementations, the one or more occlusion structures partially obstructs the flow of blood such that the blood flow rate is 20-80% of a non-occluded blood flow rate. In some implementations, the method further comprises receiving, from one or more sensors, a signal representing a measured blood pressure in the vasculature of the patient; and based on the measured blood pressure, adjusting an occlusion percentage in the vasculature of the patient caused by one or more occlusion structures of the catheter.

In some implementations, the one or more occlusion structures is configured to at least partially obstruct the flow of blood within the vasculature. In some implementations, a catheter length is between 50-100 centimeters. In some implementations, a sheath size is 7, 10, or 12 French. In some implementations, the guide wire diameter is between 0.033 and 0.040 inches. In some implementations, the occlusion structure diameter (e.g., a balloon) is between 5-30 millimeters, e.g., inflatable between 5-30 millimeters.

In some implementations, occlusion structure diameter is between 9-26 millimeters. In some implementations, occlusion structure diameter is between 10-50 millimeters. In some implementations, the occlusion structure volume (e.g., for a balloon) is between 3-60 milliliters. In some implementations, the occlusion structure volume (e.g., for a balloon) is about 25-30 milliliters. In some implementations, the catheter and/or one or more uninflated balloons can have an outside diameter of about 0.050 to 0.200 inches, e.g., 0.095 inches (7.24 French). In some implementations, these various ranges of sizes and volumes of the catheter and/or occlusion structures may partially obstruct the flow of blood within the vasculature by producing a vessel occlusion ranging from 20%-80%, depending on the catheter and/or occlusion structure dimensions.

In some implementations, the method includes receiving, from one or more sensors, a signal representing a measured $pO_2$ in the vasculature of the patient; based on the measured $pO_2$, adjusting a concentration of oxygen in the gas-enriched liquid; and delivering the gas-enriched liquid having the adjusted concentration of oxygen to the region of the vasculature of the patient.

In some implementations, the method includes adjusting both the concentration of gas in a gas-enriched liquid and the occlusion percentage in the vasculature of the patient.

In some implementations, the gas-enriched liquid is formed in the gas-enrichment chamber by mixing gas withdrawn from the patient with an atomized liquid. In some implementations, the gas-enriched liquid comprises a supersaturated oxygen liquid. In some implementations, the supersaturated oxygen liquid has an $O_2$ concentration of 0.1-6 ml $O_2$/ml liquid (STP). In some implementations, the gas-enriched liquid comprises a supersaturated oxygen enriched liquid.

In an aspect, a process includes inserting a first catheter into a vasculature of the patient, the first catheter comprising an occlusion structure configured to partially obstruct a flow of blood within the vasculature of the patient; inserting a second catheter into the vasculature of a patient, the second catheter comprising one or more lumens configured to receive gas-enriched liquid from a source of a gas-enriched liquid; delivering the gas-enriched liquid to a region of the vasculature of the patient through the one or more lumens of the second catheter; and controlling the occlusion structure of the first catheter to at least partially obstruct the flow of blood within the vasculature of the patient. The first catheter at least partially obstructs the flow of blood within the vasculature of the patient while allowing the second catheter to deliver the gas-enriched liquid to the region of the vasculature of the patient, and diverts the blood flow to the region where the gas-enriched liquid is delivered.

In some implementations of such aspects, the first catheter comprises two or more capillaries extending from a tip of the first catheter, the two or more capillaries configured to simultaneously dispense respective streams of the gas enriched liquid directly into the vasculature of the patient. In some implementations, the first catheter is configured to position the two or more capillaries at one or more predetermined angles relative to one another, such that the streams of the gas enriched liquid intersect and mix with the patient's blood. In some implementations, a controller and one or more sensors are coupled to the first and/or second catheter. The one or more sensors may be configured to measure one or more parameters of blood of the patient. Operation of the first catheter, the second catheter, or both the first catheter and the second catheter may be controlled based on the measured one or more parameters. In some implementations, the process includes receiving, from one or more sensors, a signal representing a measured blood pressure in the vasculature of the patient. In some implementations, the process includes, based on the measured blood pressure, adjusting an occlusion percentage in the vasculature of the patient caused by an occlusion structure of the catheter.

In some implementations, the process includes receiving, from one or more sensors, a signal representing a measured $pO_2$ in the vasculature of the patient. In some implementations, the process includes, based on the measured $pO_2$, adjusting a concentration of oxygen in the gas-enriched liquid. In some implementations, the process includes delivering the gas-enriched liquid having the adjusted concentration of oxygen to the region of the vasculature of the patient. In some implementations, the process includes adjusting both the concentration of gas in a gas-enriched liquid and the occlusion percentage in the vasculature of the patient. In some implementations, the gas-enriched blood is formed in the gas-enrichment chamber by mixing gas withdrawn from the patient with an atomized liquid. In some implementations, the gas-enriched liquid comprises a supersaturated oxygen liquid.

In some implementations, the supersaturated oxygen liquid has an $O_2$ concentration of 0.1-6 ml $O_2$/ml liquid (STP). In some implementations, the gas-enriched blood comprises a supersaturated oxygen enriched blood.

In an aspect, a method of treating a patient includes inserting a catheter into a vasculature of the patient, the catheter comprising one or more occlusion structures configured to at least partially obstruct a flow of blood within the vasculature of the patient and one or more lumens configured to receive gas-enriched liquid from a gas-enrichment chamber; delivering the gas-enriched liquid to a region of the vasculature of the patient through the one or more lumens of the catheter; controlling the one or more occlusion structures of the catheter to at least partially obstruct the flow of blood within the vasculature of the patient; and wherein the catheter at least partially obstructs the flow of blood within the vasculature of the patient while delivering the gas-enriched liquid to the region of the vasculature of the patient, and diverts the blood flow to the region where the gas-enriched liquid is delivered.

In some implementations, the one or more occlusion structures partially obstructs the flow of blood within the vasculature by producing a vessel occlusion of 20-80%.

In some implementations, the one or more occlusion structures partially obstructs the flow of blood such that the blood flow rate is 20-80% of a non-occluded blood flow rate.

In some implementations, the method includes receiving, from one or more sensors, a signal representing a measured blood pressure in the vasculature of the patient; and based on the measured blood pressure, adjusting an occlusion percentage in the vasculature of the patient caused by one or more occlusion structures of the catheter.

In an aspect, a process includes inserting a catheter into a vasculature of the patient, the catheter comprising an occlusion structure configured to at least partially obstruct a flow of blood within the vasculature of the patient and one or more lumens configured to receive gas-enriched liquid from a source of a gas-enriched liquid; delivering the gas-enriched liquid to a region of the vasculature of the patient through the one or more lumens of the catheter; and controlling the occlusion structure of the catheter to partially obstruct the flow of blood within the vasculature of the patient. The catheter may partially obstruct the flow of blood within the vasculature of the patient while delivering the gas-enriched blood to the region of the vasculature of the patient, and may divert the blood flow to the region where the gas-enriched liquid is delivered.

In some implementations, the first catheter comprises two or more capillaries extending from a tip of the first catheter. The two or more capillaries may be configured to simultaneously dispense respective streams of the gas-enriched liquid directly into the vasculature of the patient. In some implementations, the first catheter is configured to position the two or more capillaries at one or more predetermined angles relative to one another, such that the streams of the gas-enriched liquid intersect and mix with the patient's blood. In some implementations, one or more sensors are coupled to the first and/or second catheter. The one or more sensors may be configured to measure one or more parameters of blood of the patient. Operation of the first catheter, the second catheter, or both the first catheter and the second catheter are controlled based on the measured one or more parameters. In some implementations, the process includes receiving, from one or more sensors, a signal representing a measured blood pressure in the vasculature of the patient. In some implementations, the process includes, based on the measured blood pressure, adjusting an occlusion percentage in the vasculature of the patient caused by an occlusion structure of the catheter.

In some implementations, the process includes receiving, from one or more sensors, a signal representing a measured $pO_2$ in the vasculature of the patient. In some implementations, the process includes, based on the measured $pO_2$, adjusting a concentration of oxygen in the gas-enriched liquid. In some implementations, the process includes delivering the gas-enriched liquid having the adjusted concentration of oxygen to the region of the vasculature of the patient. In some implementations, the process includes adjusting both the concentration of gas in a gas-enriched liquid and the occlusion percentage in the vasculature of the patient. In some implementations, the gas-enriched blood is formed in the gas-enrichment chamber by mixing gas withdrawn from the patient with an atomized liquid.

In some implementations, the one or more occlusion structures is configured to at least partially obstruct the flow of blood within the vasculature. In some implementations, a catheter length is between 50-100 centimeters. In some implementations, a sheath size is 7, 10, or 12 French. In some implementations, the guide wire diameter is between 0.033 and 0.040 inches. In some implementations, the occlusion structure diameter (e.g., a balloon) is between 5-30 millimeters, e.g., inflatable between 5-30 millimeters. In some implementations, occlusion structure diameter is between 9-26 millimeters. In some implementations, occlusion structure diameter is between 10-50 millimeters. In some implementations, the occlusion structure volume (e.g., for a balloon) is between 3-60 milliliters. In some implementations, the occlusion structure volume (e.g., for a balloon) is about 25-30 milliliters. In some implementations, the catheter and/or one or more uninflated balloons can have an outside diameter of about 0.050 to 0.200 inches, e.g., 0.095 inches (7.24 French). In some implementations, these various ranges of sizes and volumes of the catheter and/or occlusion structures may partially obstruct the flow of blood within the vasculature by producing a vessel occlusion ranging from 20%-80%, depending on the catheter and/or occlusion structure dimensions.

The details of one or more embodiments are set forth in the accompanying drawings and the description. Other features and advantages will be apparent from the description and drawings, and from the claims.

DETAILED DESCRIPTION

Described herein are various systems, methods, and catheters for delivering gas-enriched blood or gas-enriched liquid within the vasculature of a patient while partially obstructing a flow of blood within the vasculature of the patient. The systems include one or more occlusion structures for partially occluding a blood vessel and thereby partially obstructing blood flow, and one or more catheters for delivering gas enriched blood, e.g., supersaturated oxygen ($SSO_2$) enriched blood, or gas-enriched liquid to a patient's vasculature. Benefits from combining a delivery of a gas enriched blood or liquid infusion with partial vessel occlusion results in a targeted local oxygenation of the heart and brain, as the partial vessel occlusion diverts blood flow to the regions where the gas enriched blood or liquid is delivered, e.g., to the heart and the brain. The combined therapy results in improved oxygenation, metabolism, and overall hemodynamic function in those regions. Also, the partial occlusion still allows some blood flow through the partially occluded vessel (e.g., the aorta), around the occlusion structure rather than fully obstructing blood flow through the vessel.

Figure 1:
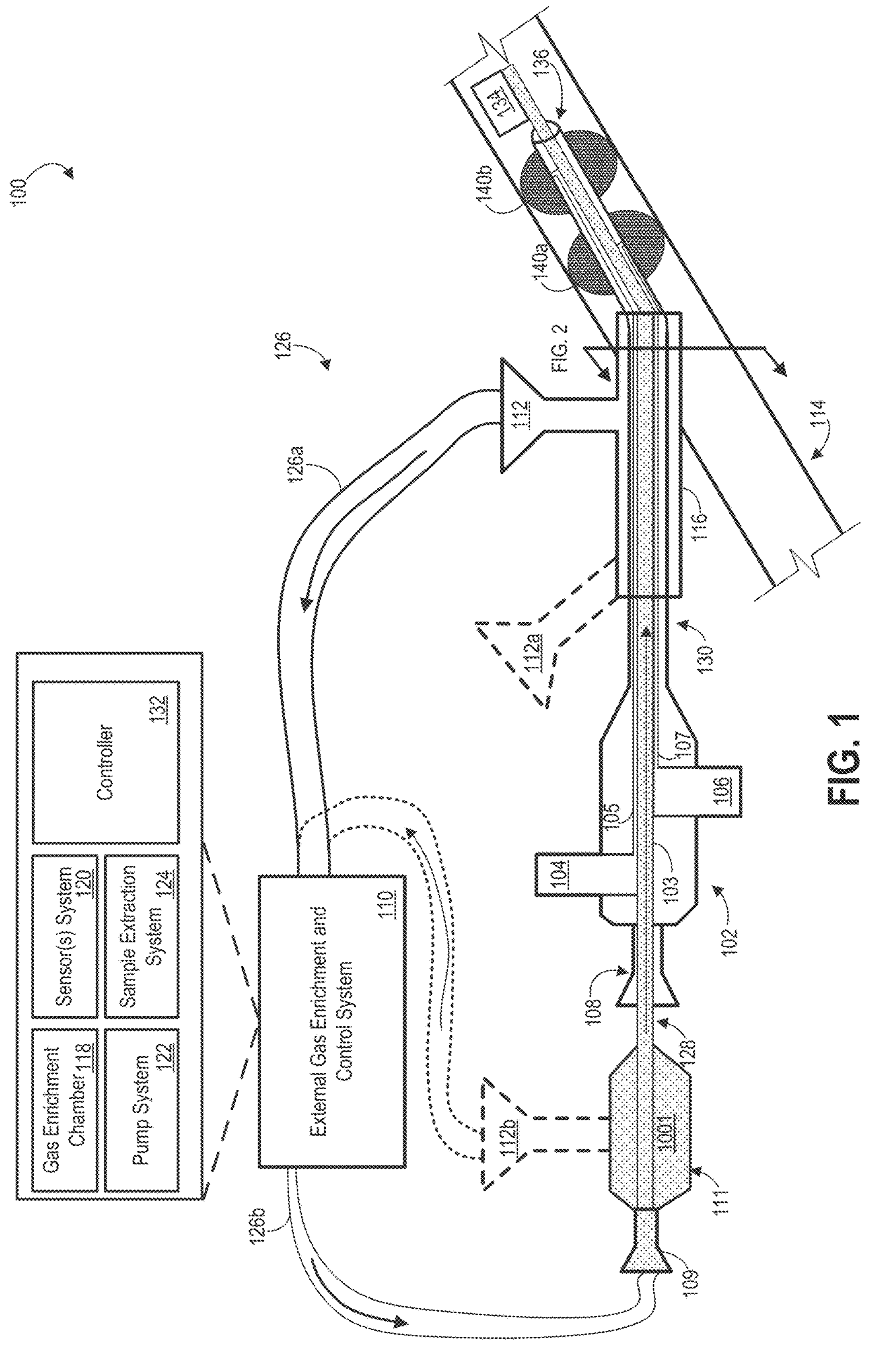
FIG. 1 is a diagram of an example system for delivering gas-enriched blood within the vasculature of a patient.

FIG. 1 shows an example system 100 for enriching a bodily fluid with a dissolved gas or gas enriched liquid, and delivering the gas enriched bodily fluid, e.g., blood, to the vasculature of a patient while also at least partially obstructing a flow of blood within the vasculature of the patient. As an example, the system 100 can be used to create a gas enriched blood by enriching a patient's blood with a gas enriched liquid, e.g., oxygen enriched liquid, in an extracorporeal gas-enrichment and control system 110 to form gas enriched blood, e.g., oxygen enriched blood, and deliver the gas enriched blood to a patient, e.g., in the case of oxygen, delivering oxygen enriched blood to a patient, thereby increasing oxygen in the blood of the patient and diffusion of oxygen into tissue. The gas-enriched blood is delivered to the patient through a catheter to provide localized delivery of gas enriched blood to ischemic tissue in the patient. For example, $SSO_2$ therapy may deliver gas-enriched arterial blood directly to at-risk or ischemic myocardial tissue, increasing oxygen diffusion to the ischemic zone, thereby reducing endothelial swelling in the microvasculature and restoring microvascular flow.

In certain implementations, oxygen enriched liquid or solution, e.g., supersaturated oxygen liquid or solution, may include liquid having a dissolved $O_2$ concentration of 0.1 ml $O_2$/ml liquid (STP) or greater or 0.1-6 ml $O_2$/ml liquid (STP) or 0.2-3 ml $O_2$/ml liquid (STP) (e.g., without clinically significant gas emboli). When such supersaturated oxygen liquid or solution is mixed with blood, the resulting blood may be referred to as supersaturated oxygen enriched blood. In certain implementations, the system 100 may deliver an infusion of supersaturated oxygen enriched blood having an elevated $pO_2$ in a target range of 400 mmHg (50 kPa) or greater or 600-1500 mmHg (80-200 kPa) or 760-1200 mmHg (100-160 kPa) or around 1000 mmHg (133 kPa).

In one example, supersaturated oxygen enriched blood may have a $pO_2$ of 760-1500 mmHg (100-200 kPa) when a source blood delivered to the gas enrichment system for mixing with a supersaturated oxygen liquid or solution has a minimum $pO_2$ of 80 mmHg (10.6 kPa), the blood flow rate is 50-150 ml/min, the $SSO_2$ saline flow rate is 2-5 ml/min and the dissolved $O_2$ concentration in saline is 0.2-3 ml $O_2$/ml saline (STP).

In another example, where the source blood is below 80 mmHg (10.6 kPa), the treatment objective may be to boost the blood $pO_2$ to above 80 mmHg (10.6 kPa), so the system 100 may deliver an infusion of supersaturated oxygen enriched blood having a $pO_2$ level of 80 mmHg (10.6 kPa) or greater or 80-760 mmHg (10.6-100 kPa).

The system 100 is configured to partially obstruct the flow of blood within the vasculature by producing partial vessel occlusion in a region of the vasculature of the patient (e.g., the aorta) while delivering $SSO_2$ enriched blood to a region of the vasculature (e.g., the left main coronary artery, internal carotid artery, aortic root). The system 100 controls the occlusion percentage and the oxygen level in the patient during treatment. The occlusion percentage includes how much occlusion is taking place in the vasculature of the patient. A lack of any occlusion, in which no blood is obstructed or diverted, is zero percent occlusion. Full occlusion, in which blood flow in the vasculature is completely blocked, is 100% occlusion. The system 100 may be configured for partial occlusion and delivery of $SSO_2$ fluid to a region of the vasculature that is distal to, upstream of or downstream of the partially occluded region. While partial vessel occlusion can include any percentage of occlusion greater than 0% and less than 100%, generally, the partial occlusion is between about 20-80%. In certain implementations, occlusion may be measured as a % of the cross-sectional area of a blood vessel. For example, partial occlusion may be 30-70% or 40-60% or 50-70% vessel occlusion. In some examples, vessel occlusion may be around 70% of the cross-sectional area of a blood vessel. The partial vessel occlusion results in partial obstruction of the flow of blood within the vasculature.

Alternatively, occlusion may be measured as a percent of blood flow of the non-occluded vessel. In certain implementations, a non-occluded blood flow rate may be initially measured within a non-occluded vessel using e.g., an intravascular ultrasound (IVUS) Doppler flow microprobe located at the occlusion catheter tip. The occlusion structure, e.g., balloon, is then inflated to achieve a partially obstructed blood flow having a blood flow rate that is 20-80% of the non-occluded blood flow rate. In certain implementations, the partially obstructed blood flow may have a blood flow that is be 30-70% or 40-60% or 50-70% of the non-occluded blood flow rate. The system controls the particular occlusion level in combination with controlling $SSO_2$ blood delivery to the vasculature to control the oxygen level in the blood and/or tissue of the patient. As described below, the system 100 can include a plurality of catheters that combine for performing this treatment, where a first catheter delivers gas-enriched blood to the vasculature of the patient and the second catheter partially occludes the vasculature of the patient, or a single catheter configured for both gas-enriched blood or $SSO_2$ delivery and partial occlusion.

The system 100 is configured to control the oxygen levels in the blood and/or tissues of the patient by controlling the oxygen levels in the supersaturated oxygen liquid or solution, (e.g., targeting a dissolved $O_2$ concentration in saline of 0.2-3 ml $O_2$/ml saline (STP)) and/or the flow rate of the supersaturated oxygen enriched blood delivered to the patient, e.g., by controlling the speed of the pump to achieve a target blood flow rate of 50-150 ml/min. The system 100 may be configured to titrate oxygen into liquid e.g., saline, to be mixed with blood and adjust the occlusion percentage until the desired oxygen level is achieved (e.g., as measured by a blood oxygen sensor in the patient). In an example, each of the concentration of oxygen delivered and the occlusion levels may be modulated during treatment.

To control the occlusion, as further described below, a size of a balloon, cuff or other occluding structure is controlled by a controller 132 of the system 100. The controller 132 can be part of the extracorporeal gas enrichment and control system 110 or part of another extracorporeal control system. The controller 132 is configured to adjust an inflation or pressure of the occlusion structure to control the occlusion percentage in the patient. The control of the occlusion structure may help to prevent or reduce a buildup of cytokines/clotting in the blood and prevent or reduce stasis of the blood.

As shown in FIG. 1, the system 100 includes a first catheter or an $SSO_2$ catheter 101 having, an extracorporeal gas enrichment and control system 110, and a second catheter or an occlusion catheter 130. The occlusion catheter may have a catheter hub 102. The $SSO_2$ catheter 101 may have a catheter hub 111. The extracorporeal gas enrichment system includes a gas enrichment chamber 118, e.g., gas enrichment cartridge, a sensor system 120, a pump system 122, and a sample extraction system 124 (e.g., syringe or pump), each of which are subsequently described in further detail.

The $SSO_2$ catheter 101 is configured to be inserted into a vasculature 114 of a patient and to facilitate the delivery of gas-enriched blood to a region of the vasculature of the patient. The $SSO_2$ catheter 101 includes one or more lumens (e.g., within the catheter body 128) configured to receive the gas enriched blood from the gas enrichment chamber 118 of the extracorporeal gas enrichment and control system 110. The controller 132 controls the pump 122, which is configured to draw blood from the patient into the gas-enrichment chamber 118 via first arterial line 126_a_. The first arterial line 126_a_ connects an input of the gas-enrichment chamber to a blood withdraw port of an introducer sheath 116, wherein the port is coupled to a blood withdraw lumen for withdrawing blood from the patient into the gas enrichment chamber 118. In certain implementations, the $SSO_2$ catheter hub 111, instead of the sheath 116, includes a blood withdraw port 112*b* coupled to a blood withdraw lumen for withdrawing blood from the patient into the gas enrichment chamber 118. A second arterial line 126*b* connects an outlet of the gas-enrichment chamber to the one or more lumens of the $SSO_2$ catheter to deliver the gas-enriched blood to the $SSO_2$ catheter, which delivers the blood to the vasculature of the patient.

The occlusion catheter 130 may include a catheter body 131 and one or more occlusion structures, e.g., balloons 140*a*, 140*b*, and may include one or more inflation lumens 105, 107 for delivering or withdrawing fluid to or from the balloons to inflate or deflate the balloons. For example, a first balloon lumen 105 may extend from a first balloon connector 104 or inflation port to balloon 140*a* and a second balloon lumen 107 may extend from a second balloon connector 106 or inflation port to balloon 140*b*. The first balloon lumen 105 and the second balloon lumen 107 are described in greater detail in relation to FIGS. 5-6. In some implementations, the balloon connectors 104, 106 are Luer connectors. The balloon lumens are configured to receive a fluid for controlling operation, e.g., inflation or deflation, of balloons 140*a*, 140*b*. While not shown in FIG. 1, tubing may be connected to connectors 104 and 106 through which fluid flows to inflate or delate the balloons. The tubing may be connected to the gas enrichment and control system, which may include a source of fluid for inflation, or be connected to a separate source of fluid for inflation. The occlusion catheter also includes one or more communicating lumens 103 (also called a through lumen), which is in fluid communication with the vasculature of the patient. In some implementations, the catheter body 131 can have an outer diameter ranging from 4 F to 12 F (1.33-4 mm), or for example, 5 F to 8 F (1.67-4 mm), or for example 7F (2.33 mm) (according to the French scale). In some implementations, the uninflated balloons can have an outside diameter of about 0.095 inches (7.24 French).

The occlusion catheter 130 is configured to be inserted into an introducer sheath 116 that is inserted into the vasculature 114 of the patient or alternatively may be inserted directly into the vasculature of the patient. The $SSO_2$ catheter 101 is configured to receive gas enriched liquid from the external gas enrichment and control system 110. As stated previously, the pump pumps the gas enriched liquid to the $SSO_2$ catheter 101 via the arterial line 126*b*. The $SSO_2$ catheter is inserted through a port and connector 108 of occlusion catheter hub 102 which leads to communicating lumen 103 of the occlusion catheter 130. The $SSO_2$ catheter is advanced through the communicating lumen 103 and into fluid communication with the vasculature of the patient e.g., through the communicating lumen 103, out of the distal end of the occlusion catheter 130 and into the vasculature of the patient.

An extracorporeal fluid loop 126 is formed as follows. A withdraw port or sidearm connector 112 in the introducer sheath 116 is configured to withdraw blood from the vasculature of the patient and send it to the extracorporeal gas enrichment system 110 via arterial line 126*a*. In some implementations, the withdraw blood port or connector 112 may be angled with respect to the introducer sheath body, as shown by alternative withdraw port or connector 112*a* placement. The port may be positioned in any angle relative to the sheath body. In certain implementations, connector 112, 112*a* may be a hemostat valve. Connector 112, 112*a* can include a valve for controlling fluid flow through the fluid loop 126. In certain implementations, the introducer sheath body may have an inner diameter of 8-10 F or 9 F.

The withdrawn blood is mixed with gas enriched liquid e.g., supersaturated oxygen liquid or solution, in the gas enrichment chamber to form a gas enriched blood, e.g., supersaturated oxygen enriched, blood. The pump then pumps the gas enriched blood to the $SSO_2$ catheter 101 via arterial line 126*b*, and the $SSO_2$ catheter 101 delivers the gas enriched blood to the vasculature of the patient.

As stated previously, the occlusion catheter 130 of the system 100 is configured to be inserted into the vasculature 114 of the patient (e.g., through sheath 116). In an example, the vasculature can include a femoral artery of the patient, an aorta, and so forth. The at least one communicating lumen of the occlusion catheter 130 is sized to receive the $SSO_2$ catheter. The $SSO_2$ catheter is inserted into the communicating lumen 103 of the occlusion catheter 130 and advanced through the occlusion catheter and into the vasculature of the patient. The one or more occlusion structures (e.g., balloons) of the occlusion catheter are configured to partially obstruct a flow of blood within the vasculature of the patient while allowing the $SSO_2$ catheter to deliver the oxygen enriched blood to a region of the vasculature of the patient. The partial occlusion by the occlusion catheter 130 diverts the blood flow to the region where the oxygen enriched blood is delivered. In some implementations, the occlusion catheter 130 may have a relatively stiff spine to support the $SSO_2$ catheter.

In one example, the system 100 or the other systems described herein may be configured to treat non-traumatic (non-hemorrhagic) cardiac arrest by delivering combined $SSO_2$ and partial occlusion therapy. When treating cardiac arrest, the $SSO_2$ catheter may be positioned in the lower aorta for delivery of $SSO_2$ blood, while partially occluding the aorta.

In certain implementations, when treating a patient, occlusion during therapy may cause a buildup of cytokines or other unwanted material in the aorta (or other vasculature) of the patient. The system may be configured to oscillate the size of the occlusion structure and therefor the degree of occlusion around a predetermined threshold level of occlusion, e.g., by inflating and deflating a balloon at regular intervals, to prevent or reduce cytokine buildup. The system 100 is configured to enable supersaturated oxygen enriched blood to be delivered to a location upstream, downstream or distal to the occlusion or at the location of the occluding therapy.

Figure 2:
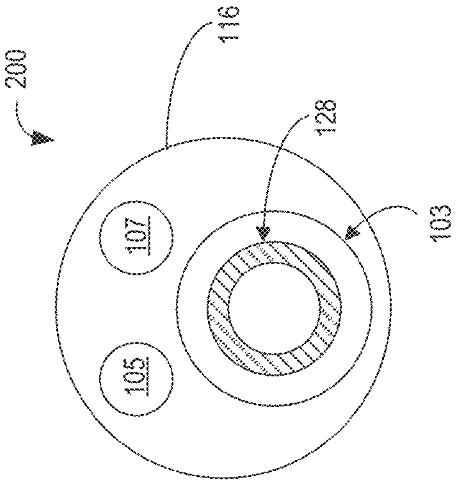
FIG. 2 is a diagram of showing a cross-section of a portion of the system of FIG. 1.

In one aspect, the occlusion structure for the occlusion catheter 130 includes one or more inflatable balloons which are sized and configured to partially occlude blood flow through an aorta. The inflation lumens 105, 107, described with reference to FIG. 1, and shown in the cross-sectional view of FIG. 2, are used to deliver or remove fluid from the balloons for inflation or deflation of the balloons. In some implementations, the occlusion structure includes a cuff around a lumen structure of the occlusion catheter 130. In some implementations, the communicating lumen 103 of the occlusion catheter 130 may be used for measuring arterial blood pressure, e.g., by advancing an arterial line through the communicating lumen in the space between the communicating lumen inner wall and the outer wall of an $SSO_2$ catheter positioned in the communicating lumen.

As discussed previously, the $SSO_2$ catheter 101 is configured to be inserted into the vasculature 114 of a patient through the occlusion catheter. In certain implementations, the $SSO_2$ catheter 101 may be inserted through the same insertion site as the occlusion catheter, but rather than being inserted through the communicating lumen 103 of the occlusion catheter, it may be advanced side-by-side with the occlusion catheter through the vasculature and past the occlusion catheter, to facilitate the delivery of a gas enriched liquid into the vasculature of the patient. In certain implementations, the $SSO_2$ catheter 101 may be inserted through a different insertion site as the occlusion catheter, e.g., the $SSO_2$ catheter may be inserted through a first insertion site into the carotid artery and the occlusion catheter is inserted through a second insertion site into the femoral artery and into the aorta. The catheter hub 102 and communicating lumen 103 of the occlusion catheter 130 is configured to facilitate the measurement of one or more parameters of the patient's blood within the patient's vasculature (e.g., by providing a sensor access to the patient's vasculature 114) and/or to facilitate the collection of blood samples from the patient's vasculature. For example, a sensor 134 may positioned on the distal end of the $SSO_2$ or occlusion catheter or in the communicating lumen of the occlusion catheter. The sensor 134 can detect various blood parameters (e.g., partial pressure of oxygen in the patient's blood ($pO_2$), the oxygen saturation of the patient's blood ($SO_2$), the flow rate of the patient's blood, a temperature of the patient's blood, and/or arterial blood pressure, during treatment or after treatment is paused or completed.

The catheter hub 102 is configured for receiving an elongated catheter body 128 of the $SSO_2$ catheter (e.g., extending along a longitudinal axis through the communicating lumen 103). In some implementations, the $SSO_2$ catheter can have a circular, elliptical, or ovular cross-section along a portion of or an entirety of its length. In some implementations, the catheter body 128 can be flexible (e.g., such that it can be bent or curved at one or more locations along its length. In some implementations, at least a portion of the $SSO_2$ catheter hub and/or the catheter body 128 can be composed of polycarbonate, glass, ceramic, stainless steel, polyether ether ketone (PEEK), polyether block amide (PEBA) (e.g., PEBAX produced by Akrema S.A., Colombes, France), acrylonitrile butadiene styrene (ABS), polyimide, and/or other suitable materials. In some implementations, the catheter body 128 can have an outer diameter ranging from 3 F to 12 F, or for example, 4 F to 6 F, or for example 5F (according to the French scale).

In some implementations, a cannula (not shown) may be inserted into the port 112 to withdraw blood from the patient and deliver the blood to the gas-enrichment chamber 118.

The occlusion catheter 130 includes multiple lumens extending through the catheter body, as shown in the cross-section view of the occlusion catheter 130 in FIG. 2. In FIG. 2, the cross-sectional view of the occlusion catheter 130 shows the communicating lumen 103 extending through a center of the catheter body (e.g., along the longitudinal axis). At least two additional lumens, e.g., inflation lumens 105, 107, may extend through opposing sides of the catheter body (e.g., parallel to the communicating lumen 103). Each of the lumens 105,107 can have a circular, elliptical, or ovular cross-section along a portion of or an entirety of its length. In some implementations, the communicating lumen 103 can have an inner diameter ranging from 0.020 inches to 0.045 inches.

Each of the lumens may include a respective input aperture and a respective output aperture. For example, the communicating lumen 103 includes an input aperture at port 108 of the catheter hub 102 and an output aperture 136 at an opposing end of the catheter body.

During an example usage of the system 100, the gas enrichment chamber 118 and the pump system 122 are coupled to the catheter hub 111 of the $SSO_2$ catheter 101, such that the gas enrichment chamber 118 is in fluid communication with the input port 109 of the catheter hub 111 via second arterial line **126*b*. As an example, one or more fluid-tight tubes can be used to convey gas enriched blood from the gas enrichment chamber 118 to the pump 122, and from the pump 122 to the input port 109. In some implementations, one or more fluid-tight tubes can be used to convey gas enriched blood from the gas enrichment chamber 118 to the input port 109, where at least a portion of the one or more fluid-tight tubes are coupled to a peristaltic pump or form part of the peristaltic pump, which urges fluid from the gas enrichment chamber to the input port 109. In some implementations, the tube can be secured to the input port 109** using a fitting or connector, such as a standard Luer connector or high-pressure Luer fitting.

In some implementations, the gas enrichment chamber 118 can include one or more storage tanks for storing the gas enriched liquid. In some implementations, the gas enriched liquid can be a supersaturated oxygen liquid or solution (e.g., saline with a dissolved $O_2$ concentration in saline of 0.2-3 ml $O_2$/ml saline (STP)) or the gas enriched liquid can be a supersaturated oxygen enriched blood, e.g., blood mixed with a supersaturated oxygen solution, e.g., saline, and having a resulting blood $pO_2$, of 760 mmHg (100 kPa) or greater, or 760-1500 mmHg (100-200 kPa). In some implementations, the gas enrichment chamber 118 includes an oxygenation device, which is operated by a console or hardware which controls operation of the oxygenation device. The console or hardware component may include a controller, processor, memory and associated circuitry. The oxygenation device may include a fluid supply chamber for receiving a physiologic liquid e.g., saline from an IV bag, and an atomization chamber for receiving a suitable gas, e.g., oxygen from an oxygen tank. The saline is pumped into the oxygen-pressurized atomization chamber and atomized to create gas-enriched or supersaturated oxygen liquid or solution, e.g., supersaturated oxygen saline or super-oxygenated saline. The supersaturated oxygen liquid or solution is mixed with blood withdrawn from the patient in a mixing chamber of the gas enrichment chamber before being sent to the patient.

A portion of the $SSO_2$ catheter 101 is inserted into a patient, such as a distal end of the catheter body 128, and positioned within a vasculature 114 of a patient (e.g., a blood vessel, such as a vein or artery). After the catheter 101 has been inserted into the patient, the pump 122 is activated, such that it draws the gas enriched blood from the gas enrichment chamber 118, and pumps the gas enriched blood, e.g., supersaturated oxygen enriched blood, through the arterial line **126*b* and into lumen 129** of the $SSO_2$ catheter.

As discussed previously, the $SSO_2$ catheter may be inserted into the patient through the communicating lumen 103 of the occlusion catheter. The communicating lumen 103 provides access to the vasculature of the patient. For example, in some implementations, a sensor 134 can be at least partially inserted into the communicating lumen 103, such that it is in fluid communication with the blood of the patient. In other implementations, the sensor may be located outside of the communicating lumen or on a catheter wall of the $SSO_2$ catheter 101 or occlusion catheter 130. The sensor 134 can obtain one or more sensor measurements regarding the blood and provide feedback regarding measured parameters affected by the $SSO_2$ therapy in order to optimize the $SSO_2$ therapy. For example, the sensor 134 can measure a partial pressure of oxygen of the patient's blood, an oxygen concentration or $SO_2$ of the patient's blood, a pressure of the patient's blood, e.g., arterial blood pressure, a flow rate of the of the patient's blood, and/or a temperature of the of the patient's blood.

Examples of such sensors include the following.

One example of a sensor for measuring a partial pressure ($pO_2$) of oxygen or oxygen saturation $SO_2$ in the patient's blood is a pulse oximeter. A pulse oximeter may be used for estimating arterial $pO_2$ or $SO_2$. Pulse oximetry estimates the percentage of oxygen bound to hemoglobin in the blood. A pulse oximeter uses light-emitting diodes and a light-sensitive sensor to measure the absorption of red and infrared light. In another example, a sensor for measuring partial pressure of oxygen comprises an electrode such as a Clark electrode for measuring $pO_2$. A Clark electrode is an electrode that measures ambient oxygen concentration in a liquid using a catalytic platinum surface according to the net reaction $O_2+4\ e^-+4\ H^+\rightarrow 2\ H_2O$. The various sensors may be coupled to a controller of the system via a cable or other wired connection or via a wireless connection.

The processor of controller 132 can receive the signals from these sensors, which signals correspond to the measured values of $pO_2$. The processor compares the measured $pO_2$ to a target range of blood $pO_2$, e.g., 760-1500 mmHg (100-200 kPa). The target range can be calculated based on a source input blood $pO_2$ of 80 mmHg (10.6 kPa), a blood flow rate of 50-150 ml/min, an $SSO_2$ saline flow rate of 2-5 ml/min and dissolved $O_2$ concentration in saline of 0.2-3 ml $O_2$/ml saline (STP). The controller can adjust any of the above parameters based on the measured $pO_2$ in blood to achieve an arterial blood $pO_2$ within the target range. The processor may generate an alert, e.g., through a user interface, audible alarm and/or visual alarm that indicates the level of $pO_2$. The measured $pO_2$ indicates the effectiveness of the supersaturated oxygen therapy, letting the caregiver know if the $pO_2$ in blood is within the target range for optimizing the delivery of oxygen to the patient's ischemic tissue. In certain implementations, the processor may control the delivery of supersaturated oxygen therapy by modifying one or more of the above referenced saline or oxygen parameters based on the signals received from the sensors.

Another example of a sensor is an $O_2$ fluorescence probe. The fluorescence probe may be coupled to a controller of the system via a cable or other wired or wireless connection. A light source of the $O_2$ fluorescence probe is illuminated. A fiber optic cable can be used to provide light to the light source in certain implementations, where the fiber optic cable is connected to the controller of the system. The fluorescence of a sensor molecule of the $O_2$ fluorescence probe is measured. The sensor molecule can include fluorophore. A signal is received by the processor from the $O_2$ fluorescence probe based on the fluorescence measurement. Fluorescence is measured by measuring the lifetime or decay of the fluorescence intensity signal from the illuminated sensor molecule (e.g., fluorophore) on the fluorescence probe. The decay of this signal is caused by the quenching effect of oxygen molecules in the blood or in tissue on the fluorescence intensity signal of the sensor molecule. The processor can determine the oxygen concentration, $SO_2$ or $pO_2$ in blood or tissue based on the quenching effect of oxygen on the florescence intensity signal of the florescence probe. Changes in a time that is required for the signal to decay due to oxygen quenching are indicative of the local oxygen concentration, $SO_2$ or $pO_2$ in blood or tissue. The processor generates an alert, e.g., through a user interface, audible alarm and/or visual alarm, based on the determined oxygen concentration, $SO_2$ or $pO_2$ in blood or tissue. The alert may indicate the effectiveness of the supersaturated oxygen therapy. The determined oxygen concentration, $SO_2$ or $pO_2$ indicates the effectiveness of the supersaturated oxygen therapy, letting the caregiver know if the oxygen concentration, $SO_2$ or $pO_2$ in blood is within a predefined target range (e.g., the expected range for a healthy individual) for optimizing the delivery of oxygen to the patient. In certain implementations, the processor may control the delivery of supersaturated oxygen therapy by modifying one or more of the saline or oxygen parameters, e.g., saline flow rate or dissolved $O_2$ concentration in saline, based on the determined oxygen concentration, $SO_2$ or $pO_2$ values.

Another example of a sensor is a temperature sensor located on or in the $SSO_2$ catheter 101 or occlusion catheter 130. For example, a thermistor may be utilized to measure the blood temperature of the patient. The processor can receive signals from the thermistor, which signals correspond to the measured values of the blood temperature. The processor may generate an alert, e.g., through a user interface, audible alarm and/or visual alarm that indicates the blood temperature, which may alert the caregiver of a hypothermic or hyperthermic, e.g., febrile, state of the patient.

An example sensor for measuring an arterial pressure of the patient's blood includes a pressure sensor positioned in or coupled to the communicating lumen 103. The communicating lumen may be used for direct measurement of arterial pressure. The communicating lumen may be connected to a fluid-filled system, which is connected to an electronic pressure transducer. A change in detected blood pressure may be indicative of improved perfusion and/or restored flow in ischemic tissue as a result of the $SSO_2$ therapy. The therapy may result in improved heart function. In certain implementations, the processor may control the delivery of supersaturated oxygen therapy based on the arterial pressure feedback.

An example sensor used to determine a blood flow rate includes a temperature sensor, e.g., a thermistor, thermocouple or thermal anemometer. A temperature sensor may be located on a catheter tip or in the communicating lumen. The temperature sensor may be heated, such that the sensor temperature is raised. As blood flows past the temperature sensor, the degree to which the temperature sensor cools down is indicative of the flow rate past the temperature sensor. The determined blood flow rate may be fed back to the system and may be indicative of the efficacy of the $SSO_2$ therapy, which results in improved perfusion and/or restored flow in ischemic tissue. In certain implementations, the processor may control the delivery of supersaturated oxygen therapy based on the blood flow rate feedback. In another example, blood flow may be measured using an ultrasonic blood flow probe, e.g., an ultrasonic perivascular blood flow probe, (e.g., Transonic PS-Series). The blood flow probe may be located in the communicating lumen, on a distal portion of the $SSO_2$ delivery catheter or occlusion catheter, or separate from either catheter.

If the sensor 134 includes a pressure sensor, the sensor may detect a pressure differential between ambient pressure and arterial pressure or an absolute value of arterial pressure. The pressure sensor may be placed anywhere in the communicating lumen but does not necessarily have to be positioned in the communicating lumen, and can be located outside of the lumen. In a catheter having multiple communicating lumens, a pressure sensor may be located in a first communicating lumen providing an uninterrupted pressure signal while blood sampling may be performed via a second communicating lumen simultaneously. In another example, two pressure sensors can be used, with one located in a first communicating lumen and one located in a second communicating lumen to provide redundancy of pressure readings.

The controller 132 of the system 100 is configured to receive one or more signals representative of the measured one or more parameters from the sensor 134. Based on the one or more signals, the controller is configured to control operation of the catheter(s) 101 or 130. For example, the controller 132 may adjust an occlusion percentage caused by the occlusion structure 140*a-b* of the occluding catheter 130. The controller 132 may adjust a concentration of gas in the gas-enriched liquid to be mixed with blood. In an example, the controller 132 may adjust both the occlusion percentage and the enriched liquid oxygen concentration. The controller 132 may be configured to receive one or more signals representative of the measured one or more parameters from the one more sensors 134. As previously described, the one or more parameters include a blood pressure in the patient e.g., arterial blood pressure. Based on the blood pressure data, the controller 132 may adjust an occlusion percentage caused by the occlusion structure 140*a-b* (e.g., balloon) of the occluding catheter 130. Adjusting the occlusion caused by the occlusion structure 140*a-b* may include increasing the occlusion to a threshold or target occlusion percentage in an initial control phase (e.g., by inflating the balloon). The controller 132, in a subsequent control phase, may be configured to gradually reduce the occlusion until the blood pressure is within a target range. The target range of the blood pressure can depend on the particular patient or treatment being performed.

In some implementations, the one or more occlusion structures is configured to at least partially obstruct the flow of blood within the vasculature. In some implementations, a catheter length is between 50-100 centimeters. In some implementations, a sheath size is 7, 10, or 12 French. In some implementations, the guide wire diameter is between 0.033 and 0.040 inches. In some implementations, the occlusion structure diameter (e.g., a balloon) is between 5-30 millimeters, e.g., inflatable between 5-30 millimeters. In some implementations, occlusion structure diameter is between 9-26 millimeters. In some implementations, occlusion structure diameter is between 10-50 millimeters. In some implementations, the occlusion structure volume (e.g., for a balloon) is between 3-60 milliliters. In some implementations, the occlusion structure volume (e.g., for a balloon) is about 25-30 milliliters. In some implementations, the catheter and/or one or more uninflated balloons can have an outside diameter of about 0.050 to 0.200 inches, e.g., 0.095 inches (7.24 French). In some implementations, these various ranges of sizes and volumes of the catheter and/or occlusion structures may partially obstruct the flow of blood within the vasculature by producing a vessel occlusion ranging from 20%-80%, depending on the catheter and/or occlusion structure dimensions.

As previously described, the sensor 134 can include a pressure-measuring device operable to measure blood pressure in the vasculature upstream or downstream of the occlusion structure of occlusion catheter 130. The pressure-measuring device may include a pressure tube inserted through the communicating lumen 103 in the occlusion catheter 130. The communicating lumen is in fluid communication with the vasculature 114 of the patient. The pressure tube may be proximally connected to a pressure monitor and may communicate with an opening of communicating lumen at the distal end. In some implementations, the pressure-measuring device is a manometer coupled proximally to a pressure monitor, and coupled to the occlusion catheter via communicating lumen 103 or mounted at a distal end of the occlusion catheter.

The controller 132 may be configured to receive one or more signals representative of the measured one or more parameters from sensors 134. As stated previously, the one or more parameters may include $pO_2$ in the blood of the patient. The controller 132, based on one or more signals of the measured $pO_2$, may adjust the concentration of oxygen in the gas-enriched liquid. Adjusting the concentration of oxygen in the gas-enriched liquid may include adjusting the concentration of oxygen in the gas-enriched liquid until the $pO_2$ in blood is within a threshold range of the target $pO_2$ in the patient's blood. Adjusting the concentration of oxygen in the gas-enriched liquid may include increasing the concentration of oxygen in an initial control phase. The controller 132 may then gradually reduce the concentration in a subsequent control phase until the $pO_2$ in the patient's blood is within a $pO_2$ target range. The target $pO_2$ range can depend on the particular patient and the treatment being performed (e.g., a location of the treatment). In some implementations, the controller is configured for adjusting both the occlusion by the occlusion catheter 130 and the $SSO_2$ concentration based on the one or more signals representing one or more parameters from the sensor 134. The adjusting includes determining a target blood pressure and a target $pO_2$ in blood and causing, by the occlusion structure, the blood pressure to be within a threshold range of the target blood pressure. The adjusting also includes adjusting the concentration of oxygen in the gas-enriched liquid until the $pO_2$ in blood is within a threshold range of the target $pO_2$.

The controller 132 can be configured to adjust the occlusion caused by the occlusion structure of the occlusion catheter 130 by oscillating a size of the occlusion structure around a predetermined resulting blood pressure value, occlusion percentage value or occlusion structure size value. Constant or nearly constant changing of the size of the occlusion structure can prevent or reduce blood stasis. The oscillation of the size of the occlusion structure can also prevent cytokine buildup at or near the occlusion structure.

In certain implementations, the controller 132 is configured to determine, based on data from a sensor(s), the cerebral oxygenation of the patient. The controller 132 is configured to cause an adjustment of an oxygen concentration in the gas-enriched liquid until the cerebral oxygenation measured by a cerebral oximeter is within a threshold range of a target cerebral oxygenation level. Cerebral oximeters can obtain continuous cerebral oxygenation values using near-infrared spectroscopy (NIRS) technology. The cerebral oximeter may include one or more oximeter probes attached to a monitor cable that is connected to a cerebral oximeter monitor (which may be separate from or part of the external gas enrichment control system). In general, most cerebral oximeters can support two to four oximeter probes with respective monitor cables. Oximeter probes can be placed anywhere on the head. The oximeter probe may include a fiber optic light source and light detectors. The light source emits light wavelengths, which penetrate the skull and cerebrum. The light detectors receive the light not absorbed during the light pathway through the skull and cerebrum. The amount of oxygen present in the brain is the difference between the amount of light sent and received by the probe. This may be determined by the controller and displayed as a percentage of oxygen. The controller 132 is configured to adjust the oxygen concentration by performing an oxygen titration in the gas-enrichment chamber 118, which is in fluid communication with the $SSO_2$ catheter 128. In another example, a non-invasive regional cerebral saturation probe may be utilized. For example, a Nonin cerebral tissue (regional) oximetry system may be used to measure $rSO_2$ (cerebral oxygen saturation) or $SpO_2$, and provide feedback to the controller regarding the same. Generally, the target cerebral oxygen saturation level is between 60-80% or 65-75%.

Any of the example sensors described herein may be used as sensors in any of the systems described herein.

In some implementations, the controller 132 is a single processor or control device for controlling operation of the $SSO_2$ catheter 128 and operation of the occlusion catheter 130. In some implementations, the controller 132 includes a first controller configured to control the operation of the $SSO_2$ catheter 128 and a second, different controller configured to control the operation of the occlusion catheter 130.

Continuing with FIG. 2, the cross-section view 200 of the catheters 101, 130 shows the $SSO_2$ catheter body 128 positioned through the lumen 103 of the occlusion catheter 130. The balloon lumens 105, 107 are used to deliver gas or liquid to the occlusion balloons of the occlusion catheter 130.

Figure 3:
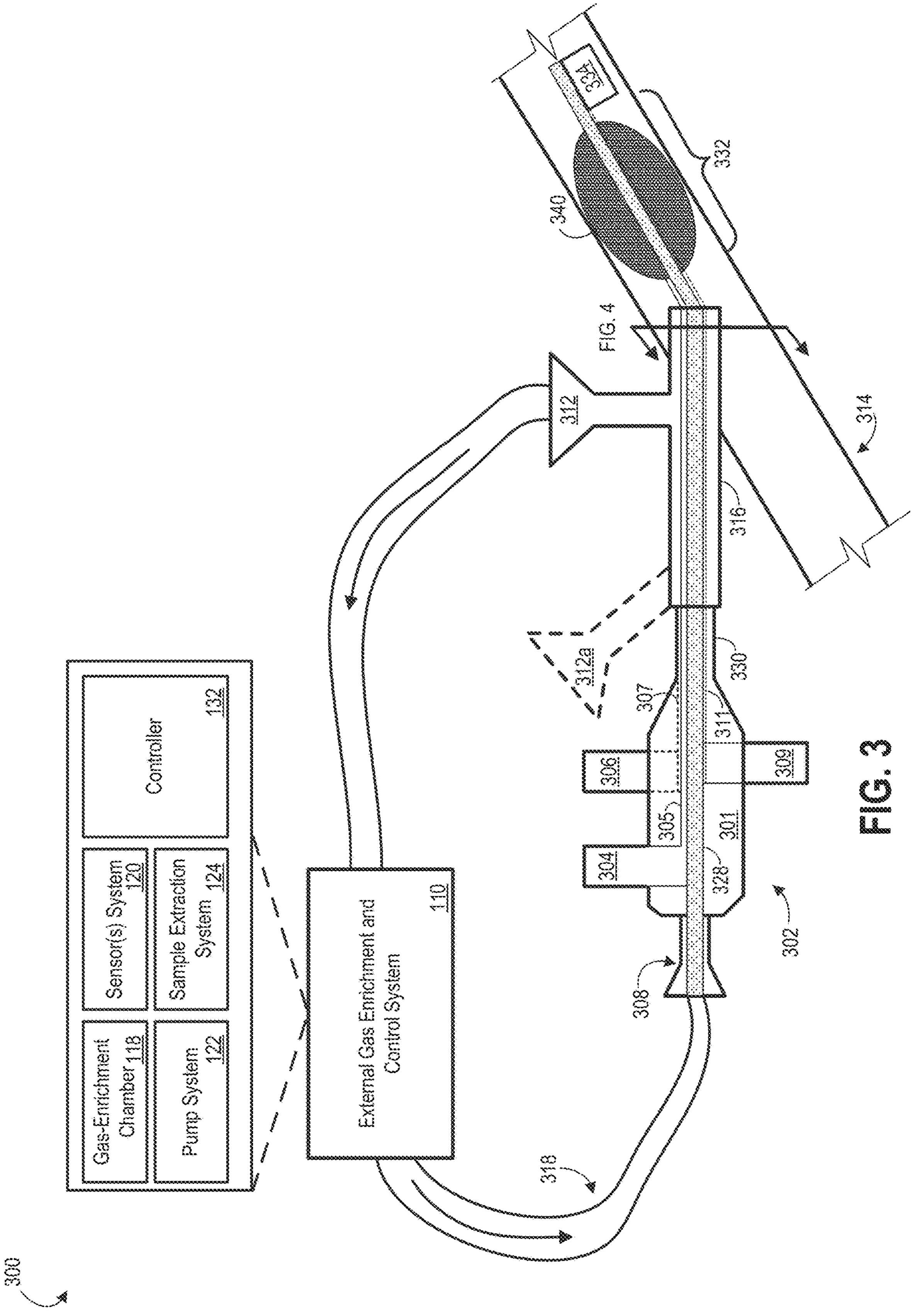
FIG. 3 is a diagram of an example system for delivering gas-enriched blood within the vasculature of a patient.

FIG. 3 shows a system 300 in which a single, integrated catheter 302 is configured for partial occlusion of a blood vessel of the patient and gas enriched liquid or $SSO_2$ blood delivery to the patient's vasculature, e.g., upstream from or downstream from the partial occlusion in the blood vessel. The integrated catheter 302 includes a catheter body 330. A first communicating lumen 328 runs through the catheter body 330 and is in fluid communication with the vasculature of the patient. The first communicating lumen 328 may be configured for supporting one or more sensors 334 (similar to sensor 134 of FIG. 1). The sensor 134 may be positioned in the first communicating lumen 328 or elsewhere on the catheter body. The communicating lumen is configured for receiving gas-enriched liquid or gas-enriched blood, e.g., $SSO_2$ blood, and delivering the same into the vasculature 314 of the patient. The first communicating lumen 328 may extend from a connector 308 or port to a distal opening or distal end of the integrated catheter The catheter 302 includes an occlusion portion 332 for partial occlusion of the vasculature 312. The integrated catheter 302 includes occlusion structure(s) 340 coupled to the catheter body 330 and configured to partially obstruct a flow of blood within the vasculature 314 of the patient while allowing the lumen to deliver the gas-enriched blood to the vasculature and to divert the blood flow to the region where the gas-enriched blood is delivered. Though one occlusion structure 340 (e.g., a balloon) is shown, the occlusion portion 332 can include two or more balloons, similar to catheter 130 of FIG. 1.

The integrated catheter 302 includes an integrated catheter hub 301. First and second occlusion or inflation lumens 305, 307 may extend from respective first and second occlusion connectors 304, 306 or ports to the one or more occlusion structures, e.g., balloon 340, in the occlusion portion 332. A second communicating lumen 311, may be configured for supporting one or more sensors and/or for receiving, extracting or sampling blood from the patient, and may extend from connector 309 or port to a distal opening or distal end of the integrated catheter. The first occlusion or inflation lumen 305 may connect a first connector 304 or port to a first occluding structure or balloon 340. The second occlusion or inflation lumen 307 may connect the second connector 306 or port to a second occluding structure or balloon (not shown) which can be optionally included on the occlusion portion 332 of the integrated catheter 302. The communicating lumen 311 and connector 309 or port may be configured for blood extraction, via a syringe, pump or other extraction system (e.g., instead of connectors 312, 312*a* of the sheath 316). In another example, a sensor 334 may be located in the communicating lumen 311 and/or the connector 309, where a sensor wire runs through the communicating lumen 311 and connector 309 and to the controller 132 to send signals to the controller.

An introducer sheath 312 may be utilized for inserting the catheter 302 into the vasculature of the patient. In certain implementations, the sheath may include a blood withdraw port 312 (or alternatively port 312*a*).). The port may be positioned in any angle relative to the sheath body. The sheath 316 is insertable into the vasculature 314. The integrated catheter body 330 can be inserted into the sheath 316. The integrated catheter hub 301 connects to the external gas enrichment and control system 110, similarly to the hubs 101, 102 previously described.

The integrated catheter 302 includes the functionality of both $SSO_2$ delivery catheter 101 and occlusion catheter 130 as described in relation to FIGS. 1-2. The integrated catheter 302 is configured to be inserted into a vasculature of a patient. A lumen 328 of the catheter body 330 extends through the catheter body and is configured to receive gas-enriched blood from a gas enrichment chamber and deliver the gas-enriched blood to a region of the vasculature of the patient. The gas-enriched blood is formed in the gas-enrichment chamber 118 by mixing blood withdrawn from the patient with a gas-enriched liquid.

As stated previously, the occlusion structure 340 can include an inflatable balloon. The catheter 302 can include a first inflation lumen 305 configured to deliver fluid into the inflatable balloon. If a second balloon is included, a second inflation lumen 307 to deliver fluid to the second balloon is included.

In some implementations, the one or more occlusion structures is configured to at least partially obstruct the flow of blood within the vasculature. In some implementations, a catheter length is between 50-100 centimeters. In some implementations, a sheath size is 7, 10, or 12 French. In some implementations, the guide wire diameter is between 0.033 and 0.040 inches. In some implementations, the occlusion structure diameter (e.g., a balloon) is between 5-30 millimeters, e.g., inflatable between 5-30 millimeters. In some implementations, occlusion structure diameter is between 9-26 millimeters. In some implementations, occlusion structure diameter is between 10-50 millimeters. In some implementations, the occlusion structure volume (e.g., for a balloon) is between 3-60 milliliters. In some implementations, the occlusion structure volume (e.g., for a balloon) is about 25-30 milliliters. In some implementations, the catheter and/or one or more uninflated balloons can have an outside diameter of about 0.050 to 0.200 inches, e.g., 0.095 inches (7.24 French). In some implementations, these various ranges of sizes and volumes of the catheter and/or occlusion structures may partially obstruct the flow of blood within the vasculature by producing a vessel occlusion ranging from 20%-80%, depending on the catheter and/or occlusion structure dimensions.

As described above and also shown in the cross-section of FIG. 4, the catheter body 330 includes a second communicating lumen 311 in fluid communication with the vasculature 314 of the patient and through which a sensor may be positioned, e.g., a sensor for measuring arterial blood pressure. For example, an arterial line, catheter or cannula connected to a pressure transducer may be used to measure pressure via the second communicating lumen 311. A pressure tube, filled with fluid, carried by the catheter and proximally connected to a pressure monitor for measuring arterial blood pressure of the patient may be included. A counter-pressure fluid bag may also be utilized with the arterial line, catheter or cannula.

Figure 4:
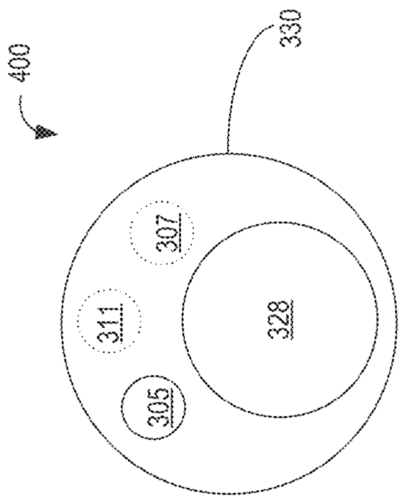
FIG. 4 is a diagram of showing a cross-section of a portion of the system of FIG. 3.

FIG. 4 shows a cross sectional view of the integrated catheter body 330. As discussed previously, the catheter body 330 includes first and second occlusion or inflation lumens 305, 307 for inflating or deflating the occluding structures or balloons of the integrated catheter 302. The catheter body 330 includes an optional sampling or second communicating lumen 311 configured for measurements via a sensor 334 or sampling blood. For example, the second communicating lumen 311 can include an arterial line for pressure measurements as described previously. The catheter body 330 includes first communicating lumen 328 for $SSO_2$ delivery that extends through the length of the integrated catheter 302. Gas enriched blood, e.g., supersaturated oxygen enriched blood, may be received from the gas enrichment chamber by the second communicating lumen and delivered by the second communicating lumen to the vasculature of the patient.

Figure 5:
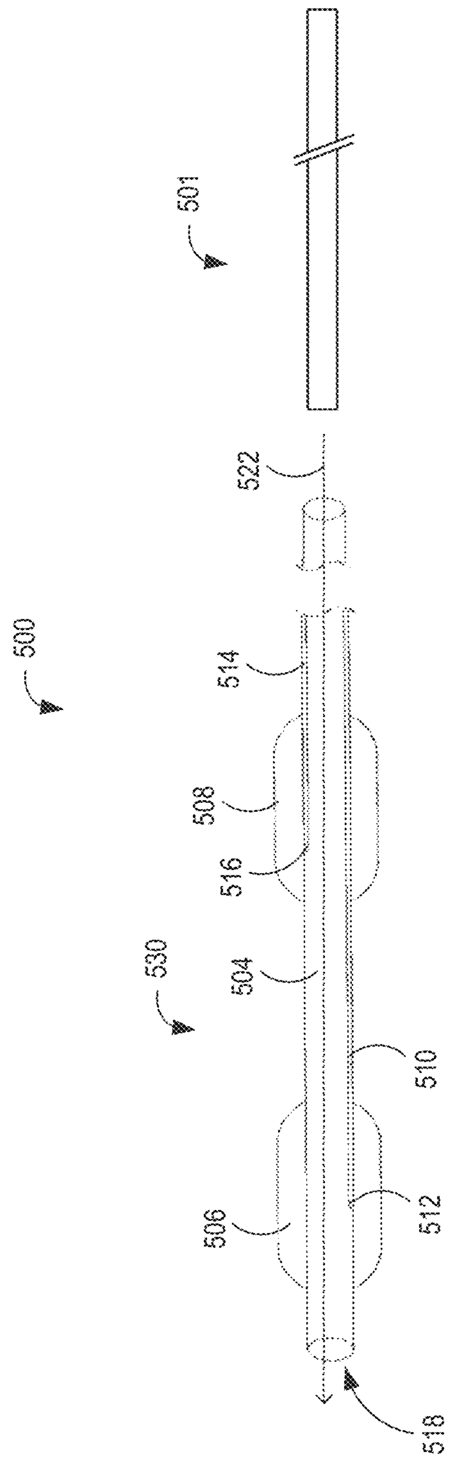
FIG. 5 is a diagram of an example catheter.

FIG. 5 shows another example system 500 for enriching a bodily fluid with a gas enriched blood inside of the vasculature of a patient while also partially obstructing a flow of blood within the vasculature of the patient. The system 500 includes a first catheter 501 configured to be inserted into the vasculature of a patient, e.g., through a communicating lumen of an occlusion catheter or separate insertion site, and to facilitate the delivery of a gas enriched blood into the vasculature of the patient. In some implementations, the first catheter or gas-enriched fluid delivery catheter 501 can be similar to one or more of the $SSO_2$ delivery catheters described above (e.g., with reference to FIGS. 1-5). Further, the first catheter 501 can be used in conjunction with an external gas enrichment control system, gas enrichment chamber, gas enriched liquid source, a pump, a sensor, a sample extraction system (e.g., syringe), as described above.

The system 500 includes a second catheter or occlusion catheter 530 for selectively occluding the flow of blood in one or more blood vessels to prioritize the flow of blood to certain portions of a patient's body over others. As examples, the occlusion catheter 530 (and the occlusion catheters described previously) can be used to treat patients suffering from global cerebral ischemia due to systemic circulatory failure, focal cerebral ischemia due to thromboembolic occlusion of the cerebral vasculature, and/or hypertension. As another example, the occlusion catheter 530 can be used to perform spinal cord conditioning on a patient.

As shown in FIG. 5, the occlusion catheter 530 includes an elongate catheter body 504 defining a communicating lumen 518. The catheter body 504 includes a distal end and a proximal end. The distal end of the catheter body 504 includes a first occlusion structure or expandable member 506 and second occlusion structure or expandable member 508. In some implementations, the occlusion structures 506 and 508 can include balloons (e.g., elongate balloons) that are spaced from each other along the catheter body 504.

In this example, the first occlusion structure 506 is in fluid communication with an inflation lumen 510 through a port 512. Gas and/or air can be directed into the first expandable member 506 through the inflation lumen 510 and the port 512, such that the first expandable member 506 is selectively inflated (e.g., to at least partially restrict the flow of blood past it). Further, gas and/or air can be withdrawn from the first expandable member 506 through the inflation lumen 510 and the port 512, such that the first occlusion structure 506 is selectively deflated.

Further, the second occlusion structure 508 is in fluid communication with an inflation lumen 514 through a port 516. Similarly, gas and/or air can be directed into the second occlusion structure 508 through the inflation lumen 514 and the port 516, such that the second occlusion structure 506 is selectively inflated (e.g., to at least partially restrict the flow of blood past it). Further, gas and/or air can be withdrawn from the second occlusion structure 508 through the inflation lumen 514 and the port 516, such that the second occlusion structure 508 is selectively deflated.

In the example shown in FIG. 5, the occlusion structures 506 and 508 are configured to be inflated independent of each other (e.g., using different respective inflation lumens). However, in some implementations, the occlusion structures 506 and 508 can be configured to be inflated using a common inflation lumen. Further, although FIG. 5 shows an occlusion catheter 530 having two occlusion structures, in practice, the catheter 504 can have any number of occlusion structures along its length (e.g., one, two, three, four, or more).

Figure 6:
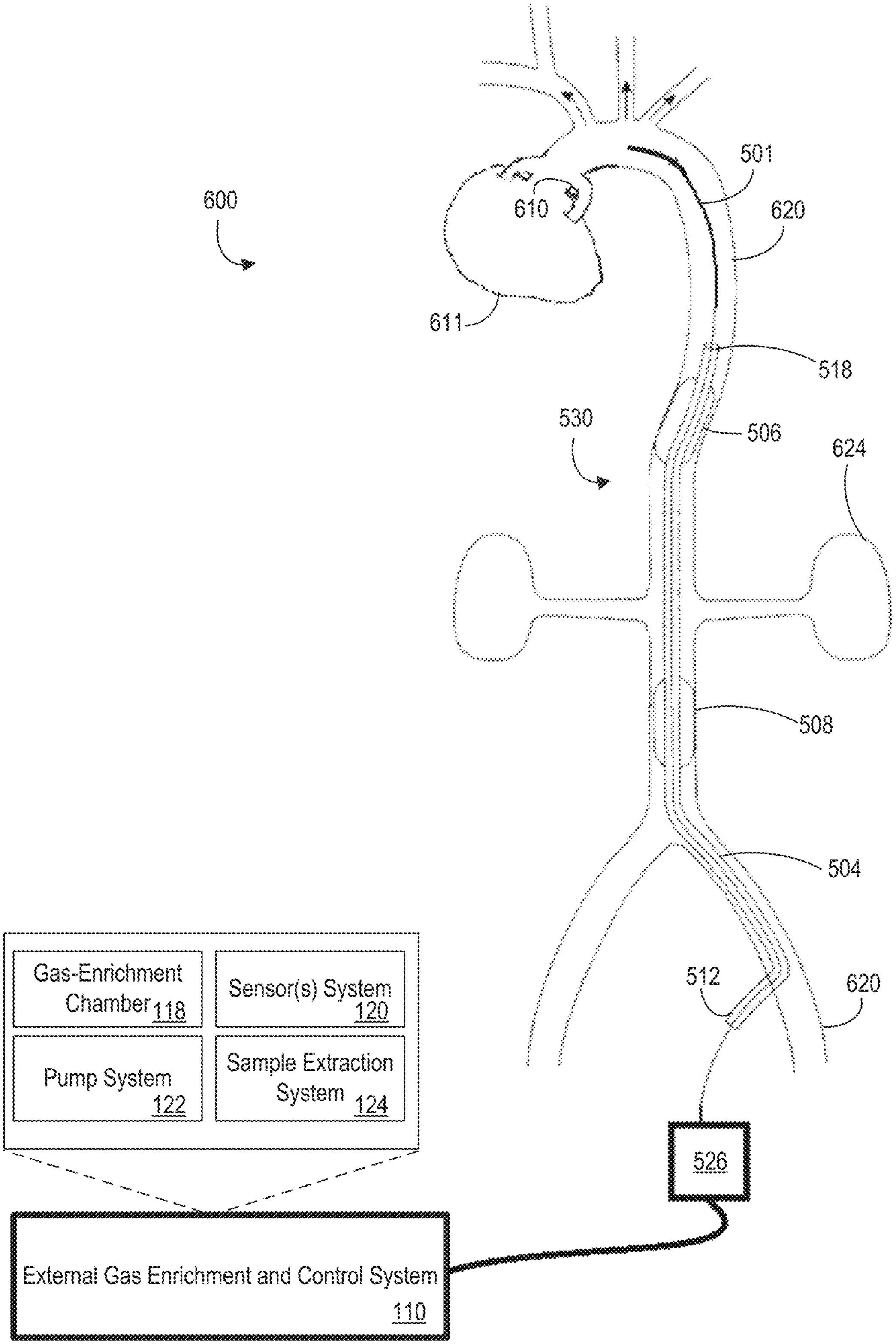
FIG. 6 is a diagram of an example catheter system.

FIG. 6 shows an example environment 600 for use of system 500 of FIG. 5. During an example usage of the system 500, the second catheter 530 is inserted in the descending aorta 620 of a patient, and advanced to a position such that the first occlusion structure 506 is upstream of the renal arteries, celiac, and superior mesenteric artery, and the second occlusion structure 508 is downstream of these arteries. In some implementations, a guidewire or stylet 622 can be inserted into the lumen 518 of the catheter 530 to facilitate the insertion and positioning of the catheter body 504.

In some implementations, the second catheter 530 having two occlusion structures 506, 508 permits independent regulation and adjustment of cerebral blood flow and renal blood flow. For example, the second occlusion structure 508 can be first expanded while measuring cerebral blood flow until the desired increase over baseline is obtained (e.g., 100% increase). This step can also result in increased blood flow to the renal and superior mesenteric arteries. If this step results in inadequate cerebral blood flow increase, then the first occlusion structure 506 can be expanded to constrict upstream the renal and superior mesenteric arteries until the desired cerebral blood flow increase is obtained. Deployment of the upstream occlusion structure 506 reduces blood flow to the renal and superior mesenteric arteries as compared with blood flow before deployment of the upstream occlusion structure 506.

In some implementations, if the deployment of downstream occlusion structure 508 produces the desired increase in cerebral blood flow, then the upstream occlusion structure 506 will not be deployed. In some implementations, the upstream occlusion structure 506 can be deployed so that constriction in downstream occlusion structure 508 is reduced, thereby partially relieving the renal and superior mesenteric arteries of increased flow. It will be understood that inclusion of an occlusion structure downstream is desirable in some cases because it allows the physician to maintain renal blood flow at or above baseline while increasing blood flow to the brain. It may also be desirable to achieve constriction predominantly downstream of the renal arteries that supply blood to kidneys 624 to avoid obstructing the spinal arteries that lie upstream the renal arteries. It may also be desirable to have both occlusion structures 506 and 508 partially inflated, rather than either balloon fully inflated, to avoid blocking arteries that branch from the aorta.

Alternatively, both occlusion structures 506 and 508 may be inflated simultaneously until a desired increase in cerebral flow is achieved. In this manner, flow to the renal arteries will be maintained at substantially the initial baseline flow. If it is desired to further adjust renal blood flow while maintaining the cerebral blood flow and/or increase in proximal aortic pressure, the two occlusion structures 506 and 508 can be simultaneously adjusted (e.g., one increased and one decreased) until the desired renal blood flow is achieved.

Referring back to FIG. 5, the first catheter 501 can be inserted into and through the lumen 518 of the second catheter 530 (e.g., from the proximal end of the occlusion structure catheter 530 to the distal end of the occlusion structure catheter 530), such that the delivery end of the first catheter 501 is positioned within a vasculature of a patient (e.g., a blood vessel, such as a vein or artery). After the first catheter 501 has been inserted into the patient, the first catheter 501 can be used to deliver a gas enriched blood, e.g., $SSO_2$ blood, into the vasculature of the patient (e.g., as described above).

Although an example positioning of the occlusion structures are shown in FIG. 6, in practice, the occlusion structures can be positioned elsewhere in the patient's vasculature to selectively direct blood to certain portions of the patient's body over others.

In the example shown in FIGS. 5 and 6, the system 500 includes a first catheter or $SSO_2$ delivery catheter 501 that is separate and distinct from the second or occlusion catheter 530, whereby the first catheter 501 is inserted into the occlusion catheter 530 during use. However, is some implementations, a system can include a single catheter that is configured to be inserted into the vasculature of a patient, and is configured to both (i) facilitate the delivery of a gas enriched blood into the vasculature of the patient, and (ii) selectively partially occlude the flow of blood in one or more blood vessels as previously described.

Continuing with FIG. 6, the occlusion catheter 530 is a partial occlusion catheter and can be placed as now described. The occlusion catheter may be placed through an introducer sheath into the femoral artery 620 over a guidewire through communicating lumen 518. The occlusion catheter 530 may be advanced until the distal end of occlusion catheter 530 resides in the aorta near the heart 611 below the arch but above the renal arteries. The occlusion catheter hub 512 has a central port for the guidewire (communicating lumen 518) and two ports for the inflation lumens 510, 514, which are in fluid communication with the occlusion structures 506, 508 (e.g., balloons). One occlusion structure is above the renal arteries, the other is below the renal arteries in the abdominal aorta. Both occlusion structures are inflated as necessary. The first catheter 501, e.g., $SSO_2$ delivery catheter, may be advanced over the guidewire through the communicating lumen 518 until it is positioned near the left coronary artery 610, secured by a hemostasis valve at the occlusion catheter hub 512. The guidewire is then removed. The external gas enrichment and control system 110 (e.g., a cartridge operated by a control console) is connected to a blood withdraw port of an introducer sheath positioned in the femoral artery 620 via a first arterial line and connected to the first catheter 501 via a second arterial line. Blood is withdrawn into the gas enrichment chamber, mixed with supersaturated oxygen liquid or solution, and the supersaturated oxygen enriched blood is then delivered to the first catheter 501 for delivery of supersaturated oxygen enriched blood to the vasculature of the patient. In other implementations, the first and second catheters may be inserted and positioned in other locations in the patient's vasculature. For example, the first catheter for delivery of $SSO_2$ blood to the patient may be positioned in the brain or pulmonary artery. The first catheter may be inserted in the patient's neck, e.g., in the jugular, while the second catheter 530 is inserted into the femoral artery and into the aorta. The $SSO_2$ catheter hub and connector 526 is connected to the control system 110 when the equipment is ready to deliver therapy.

Figure 7:
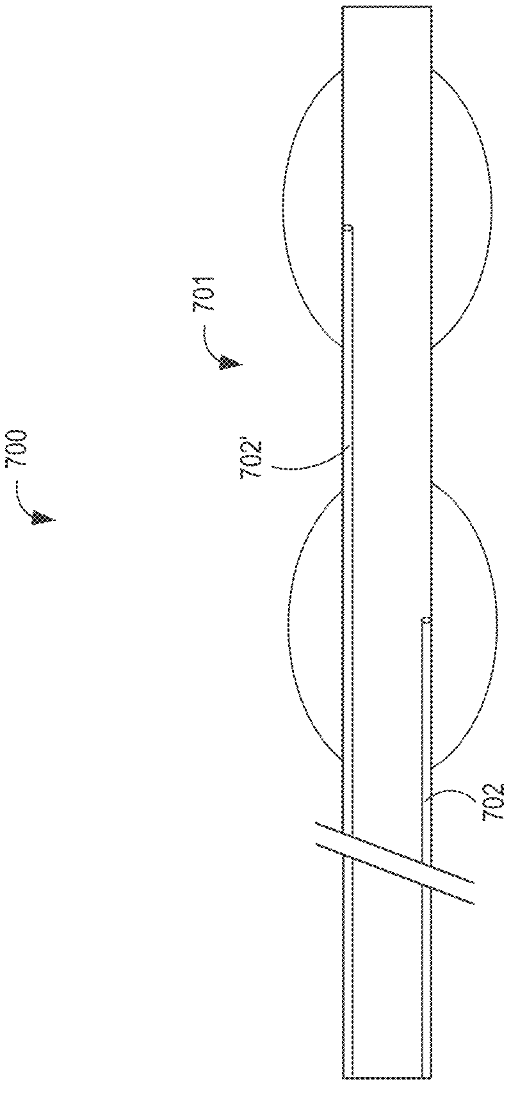
FIG. 7 is a diagram of an example catheter.

As another example FIG. 7 shows a system 700 for delivering supersaturated oxygen enriched blood to a partially occluded portion of the vasculature of a patient. The system 700 includes a catheter 701 configured to be inserted into the vasculature of a patient, and to facilitate the delivery of a gas enriched blood into the vasculature of the patient. In some implementations, the catheter 701 can be similar to one or more of the catheters described above. Further, the catheter 701 can be used in conjunction with an external gas enrichment and control system, gas enriched liquid source, a pump, a sensor, and/or a sample extraction system, as described above.

In this example, the catheter 501 also includes occlusion structures 706 and 708 for selectively occluding the flow of blood through one or more blood vessels of a patient. In some implementations, the occlusion structures s 706 and 708 can be similar to the occlusion structures described above (e.g., with reference to FIGS. 5 and 6). In some implementations, the catheter 701 can include one or more additional lumens 702, 702' extending through it to facilitate inflation or deflation of occlusion structures 506 and 508.

The entire disclosures of U.S. Pat. Nos. 6,743,196, 6,582,387, 7,820,102 and 8,246,564 are expressly incorporated herein by reference.

Figure 8:
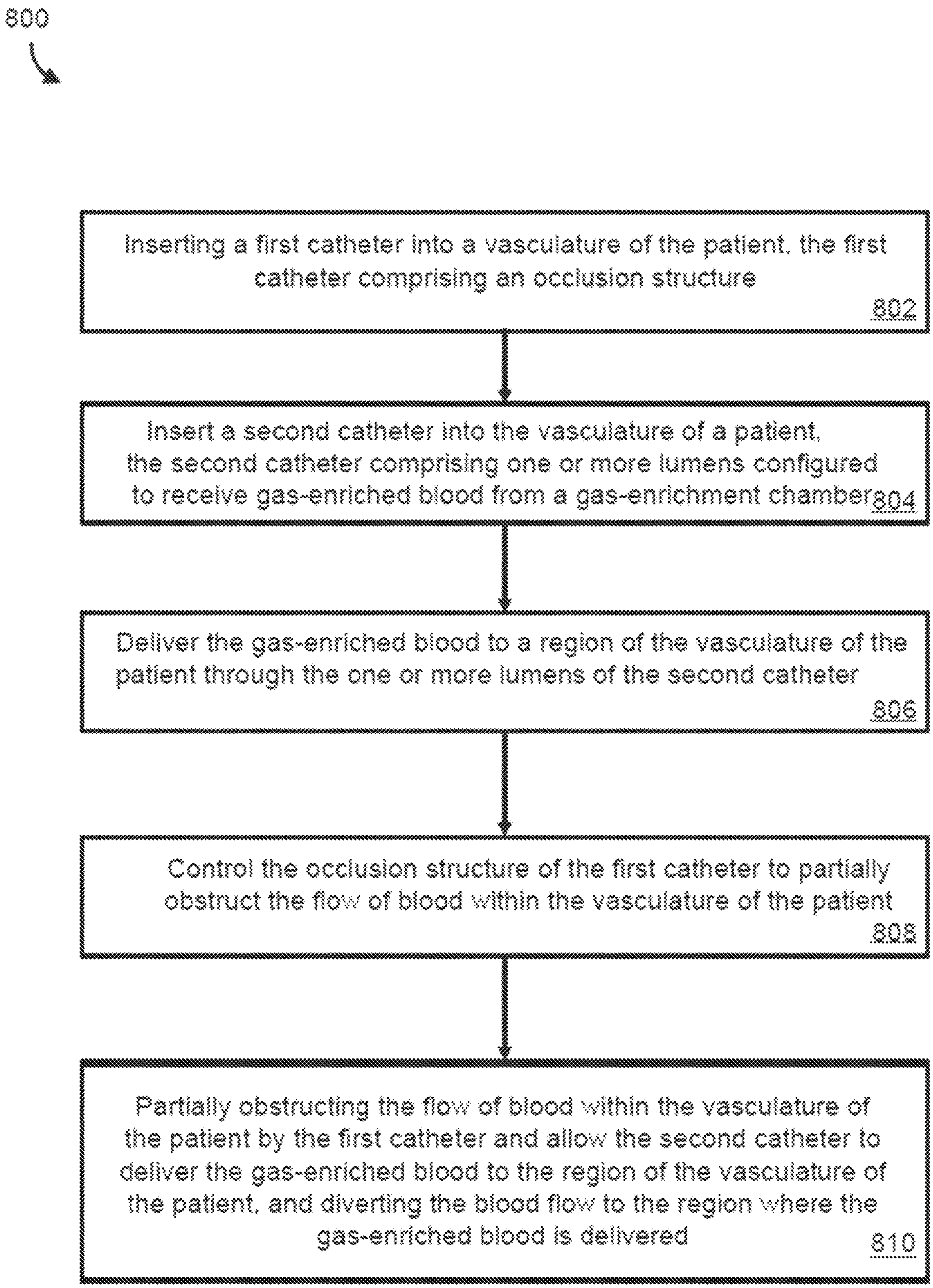
FIG. 8 shows a flow diagram including an example process for providing combined gas enrichment and partial occlusion therapy.

FIG. 8 shows a flow diagram including an example process for providing combined $SSO_2$ and partial occlusion therapy to treat a patient comprising the following steps: inserting a first catheter into a vasculature of the patient, the first catheter comprising an occlusion structure configured to partially obstruct a flow of blood within the vasculature of the patient 802; inserting a second catheter into the vasculature of a patient, the second catheter comprising one or more lumens configured to receive gas-enriched blood from a gas-enrichment chamber 804; delivering the gas-enriched blood to a region of the vasculature of the patient through the one or more lumens of the second catheter 806; and controlling the occlusion structure of the first catheter to partially obstruct the flow of blood within the vasculature of the patient 808; the first catheter partially obstructing the flow of blood within the vasculature of the patient while allowing the second catheter to deliver the gas-enriched blood to the region of the vasculature of the patient, and diverting the blood flow to the region where the gas-enriched blood is delivered 810.

Figure 9:
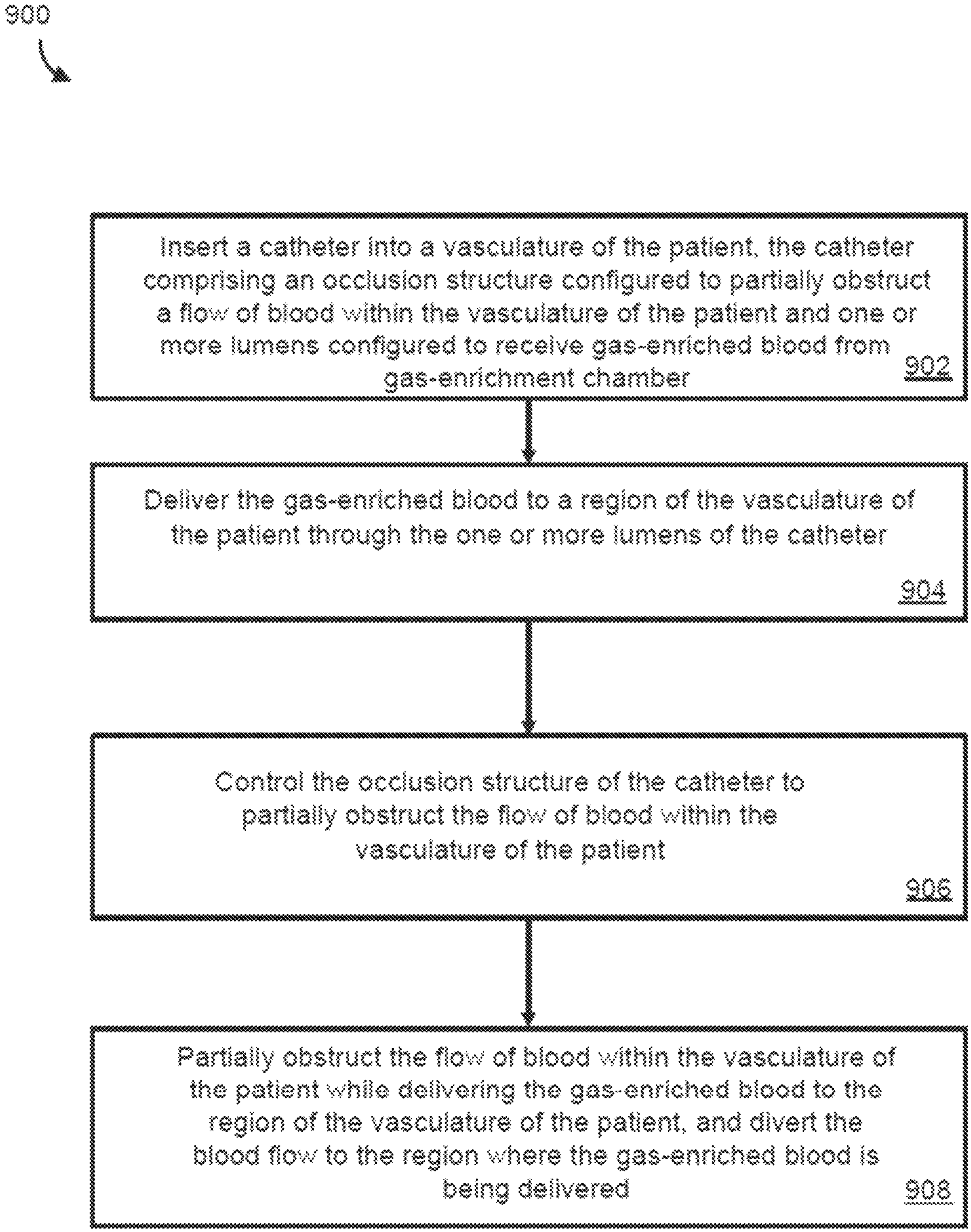
FIG. 9 shows a flow diagram including an example process for providing combined gas enrichment and partial occlusion therapy.

FIG. 9 shows a flow diagram including an example process for providing combined SSO2 and partial occlusion therapy to treat a patient comprising the following steps: inserting a catheter into a vasculature of the patient, the catheter comprising an occlusion structure configured to partially obstruct a flow of blood within the vasculature of the patient and one or more lumens configured to receive gas-enriched blood from a gas-enrichment chamber 902; delivering the gas-enriched blood to a region of the vasculature of the patient through the one or more lumens of the catheter 904; controlling the occlusion structure of the catheter to partially obstruct the flow of blood within the vasculature of the patient 906; the catheter partially obstructing the flow of blood within the vasculature of the patient while delivering the gas-enriched blood to the region of the vasculature of the patient, and diverting the blood flow to the region where the gas-enriched blood is delivered 908.

Figure 10:
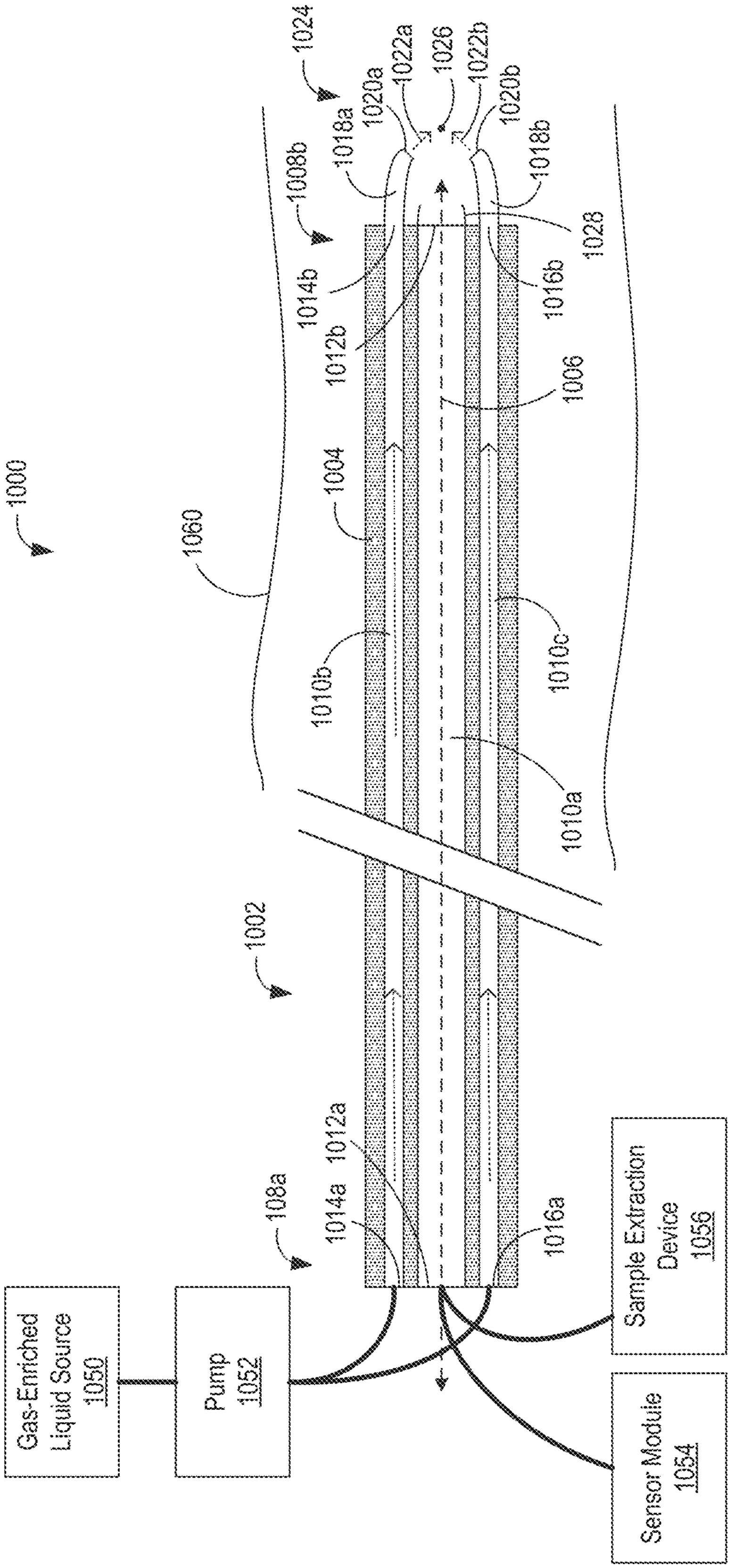
FIG. 10 is a diagram of an example system for delivering gas-enriched liquid within the vasculature of a patient.

FIG. 10 shows an example system 1000 for enriching a bodily liquid with a dissolved gas or gas enriched liquid inside of an enclosed area of a body by direct injection of the gas or gas-enriched liquid. As an example, the system 1000 can be used to enrich a patient's blood with supersaturated oxygen enriched liquid or supersaturated liquid within the vasculature of the patient thereby delivering supersaturated oxygen ($SSO_2$) therapy to a patient, increasing oxygen in the blood and diffusion of oxygen into tissue. In certain implementations, oxygen enriched liquid or solution, e.g., supersaturated oxygen enriched liquid or solution, may include liquid having a dissolved $O_2$ concentration of 0.1 ml $O_2$/ml liquid (STP) or greater or 0.1-6 ml $O_2$/ml liquid (STP) or 0.2-3 ml $O_2$/ml liquid (STP) (e.g., without clinically significant gas emboli).

As shown in FIG. 10, the system 1000 may include a catheter 1002, a gas enriched liquid source 1050, a pump 1052, and a sensor module 1054, and a sample extraction device 1056. The catheter 1002 is configured to be inserted into the vasculature of a patient, to facilitate the delivery of a gas enriched liquid (e.g., from the gas enriched liquid source 1050) into the vasculature of the patient via the pump 1052. Further, the catheter 1002 may be configured to facilitate the measurement of one or more properties of the patient's blood within the patient's vasculature (e.g., by providing the sensor module 1054 access to the patient's vasculature) and/or to facilitate the collection of blood samples from the patient's vasculature (e.g., by providing the sample extraction device 1056 access to the patient's vasculature). For example, the sensor module 1054 may be positioned on the distal (or first) end 1008_a_ of the catheter 1002 or in a communicating lumen of the catheter 1002. The sensors of the sensor module 1054 can detect various blood parameters (e.g., partial pressure of oxygen in the patient's blood ($pO_2$), the oxygen saturation of the patient's blood ($SO_2$), the flow rate of the patient's blood, a temperature of the patient's blood), during treatment or after treatment is paused or completed.

The catheter 1002 includes an elongated catheter body 1004 (e.g., extending along a longitudinal axis 1006 through the center of the catheter body 1004) having a proximal (or second) end 1008_b_ opposing the distal end 1008_a_. In some implementations, the catheter can have a circular, elliptical, or ovular cross-section along a portion of, or an entirety of, its length. In some implementations, the catheter body 1004 can be flexible (e.g., such that it can be bent or curved at one or more locations along its length. In some implementations, at least a portion of the catheter 1002 and/or the catheter body 1004 can be composed of polycarbonate, glass, ceramic, stainless steel, polyether ether ketone (PEEK), polyether block amide (PEBA) (e.g., PEBAX produced by Akrema S.A., Colombes, France), acrylonitrile butadiene styrene (ABS), polyimide, and/or other suitable materials. In some implementations, the catheter body 1004 can have an outer diameter ranging from 4 F to 12 F, or for example, 4 F to 6 F (according to the French scale—about 1.33 mm to 4 mm or about 1.33 mm to 2 mm).

Further, the catheter 1002 includes multiple lumens extending through the catheter body 1004. In this example, the catheter 1002 includes one or more communicating lumens 1010_a_ extending through a center of the catheter body 1004 (e.g., along the longitudinal axis 1006). At least two additional lumens 1010_b_ and 1010_c_ may extend through opposing sides of the catheter body 1004 (e.g., parallel to the communicating lumen 1010_a_). Each of the lumens 1010_a_-1010_c_ can have a circular, elliptical, or ovular cross-section along a portion of or an entirety of its length. In some implementations, the communicating lumen 1010_a_ can have an inner diameter ranging from 0.020 inches to 0.045 inches (about 0.5 mm to about 1.1 mm).

Each of the lumens 1010_a_-1010_c_ includes a respective input aperture and a respective output aperture. For example, the communicating lumen 1010_a_ includes an input aperture 1012_a_ on the first (or distal) end 1008_a_ of the catheter body 1004 and an output aperture 1012_b_ on the second (or proximal) end 1008_b_ of the catheter body 1004. As another example, the lumen 1010_b_ includes an input aperture 1014_a_ on the first end 1008_a_ of the catheter body 1004 and an output aperture 1014_b_ on the second end 1008_b_ of the catheter body 1004. As another example, the lumen 1010_c_ includes an input aperture 1016_a_ on the first end 1008_a_ of the catheter body 1004 and an output aperture 1016_b_ on the second end 1008_b_ of the catheter body 1004.

Further, the catheter 1002 includes a capillary 1018_a_ extending from and in fluid communication with the output aperture 1014_b_ of the lumen 1010_b_ (e.g., such that fluid can flow from the lumen 1010_b_ into the capillary 1018_a_. The capillary 1018_a_ terminates at an output aperture 1020_a_. In some implementations, the capillary 1018_a_ can have an inner diameter between 40 microns and 1000 microns. In some implementations, the capillary 1018_a_ can have an outer diameter between 140 microns and 1060 microns. In some implementations, the capillary 1018_a_ can have a length ranging from 5 cm to 10 cm or be a length "1" which is substantially equal to the diameter of the catheter tip or distal end.

The catheter 1002 also includes a capillary 1018_b_ extending from and in fluid communication with the output aperture 1016_b_ of the lumen 1010_c_ (e.g., such that fluid can flow from the lumen 1010_c_ into the capillary 1018_b_. The capillary 1018_b_ terminates at an output aperture 1020_b_. In some implementations, the capillary 1018_b_ can have an inner diameter from 40 microns to 1000 microns. In some implementations, the capillary 1018_b_ can have an outer diameter from 140 microns to 400 microns. In some implementations, the capillary 1018_b_ can have a length ranging from 5 cm to 10 cm or be a length "1" which is substantially equal to the diameter of the catheter tip or distal end.

In some implementations, the capillaries 1018_a_ and 1018_b_ may have identical or different sized inner and/or outer diameters. In some implementations, the capillaries 1018_a_ and 1018_b_ may have identical or different sized lengths.

During an example usage of the system 1000, the gas enriched liquid source 1050 and the pump 1052 are coupled to the catheter 1002, such that the gas enriched liquid source 1050 and the pump 1052 are in fluid communication with the input apertures 1014_a_ and 1016_a_ of the lumens 1010_b_ and 1010_c_, respectively. As an example, one or more fluid-tight tubes can be used to convey gas enriched liquid from the gas enriched liquid source 1050 to the pump 1052, and from the pump 1052 to the input apertures 1014_a_ and 1016_b_. In some implementations, one or more fluid-tight tubes can be used to convey gas enriched liquid from the gas enriched liquid source 1050 to the input apertures 1014_a_ and 1016_b_, where at least a portion of the one or more fluid-tight tubes are coupled to a peristaltic pump or form part of the peristaltic pump, which urges fluid from the gas enriched liquid source to the input apertures 1014$a$ and 1016$b$. In some implementations, the tubes can be secured to the input apertures 1014$a$ and 1016$b$ using a fitting or connector, such as a high-pressure Luer fitting.

In some implementations, the gas enriched liquid source 1050 can include one or more storage tanks for storing the gas enriched liquid. In some implementations, the gas enriched liquid can be a supersaturated oxygen enriched liquid or supersaturated liquid, such as a liquid having a dissolved oxygen ($O_2$) concentration between 0.2 and 3 ml $O_2$/ml solvent (which is the concentration equivalent of 1000 psi to 10500 psi-about 6.9 MPa to 720 MPa). In some implementations, the gas enriched liquid can include liquid enriched with oxygen, ozone, inert gas, nitrogen, nitrous oxide, carbon dioxide, and/or air. In some implementations, the gas enriched liquid source 1050 may include an oxygenation device, which is operated by a console or hardware component that controls operation of the oxygenation device, as described in U.S. Pat. No. 9,919,276, the entire disclosure of such patent being expressly incorporated herein by reference in its entirety. The console or hardware component may include a controller, processor, memory and associated circuitry. The oxygenation device may include a fluid supply chamber for receiving a physiologic liquid e.g., saline from an IV bag, and an atomization chamber for receiving a suitable gas, e.g., oxygen from an oxygen tank. The saline is pumped into the oxygen-pressurized atomization chamber and atomized to create gas-enriched or supersaturated liquid, e.g., supersaturated oxygen-enriched saline or supersaturated saline. In certain implementations, the gas-enriched liquid can be oxygen enriched liquid or solution, e.g., supersaturated oxygen enriched liquid or solution, may include liquid having a dissolved $O_2$ concentration of 0.1 ml $O_2$/ml liquid (STP) or greater or 0.1-6 ml $O_2$/ml liquid (STP) or 0.2-3 ml $O_2$/ml liquid (STP) (e.g., without clinically significant gas emboli). In some implementations, the gas enriched liquid can be a supersaturated oxygen enriched liquid or solution (e.g., saline with a dissolved $O_2$ concentration in saline of 0.1 ml $O_2$/ml saline (STP) or greater or 0.1-6 ml $O_2$/ml saline (STP) or 0.2-3 ml $O_2$/ml saline (STP) (e.g., without clinically significant gas emboli).

Further, a portion of the catheter 1002 is inserted into a patient, such that the second end 1008$b$ of the catheter body 1004 is positioned within a vasculature of a patient (e.g., a blood vessel 1060, such as a vein or artery). After the catheter 1002 has been inserted into the patient, the pump 1052 is activated, such that it draws the gas enriched liquid from the gas enriched liquid source 1050, and pumps the gas enriched liquid, e.g., supersaturated liquid, into each of the lumens 1010$b$ and 1010$c$. The gas enriched liquid flows through the lumens 1010$b$ and 1010$c$ and into the capillaries 1018$a$ and 1018$b$ and is expelled from the output apertures 1020$a$ and 1020$b$ as two respective streams 1022$a$ and 1022$b$.

In some implementations, the system 1000 can be configured to expel streams according to different flow rates and/or pressures. For example, the system 1000 can be configured to expel streams between 1 mL/minute (e.g., at a pressure of 1000 psi, about 6900 kPa) to 3 mL/minute (e.g., at a pressure of 300 psi, about 2 MPa).

The capillaries 1018$a$ and 1018$b$ are configured such that the streams 1022$a$ and 1022$b$ intersect with one another and mix in a mixing region 1024 within the vasculature of the patient. For example, the capillaries 1018$a$ and 1018$b$ can define respective paths that are angled relative to the longitudinal axis 1006, such that the streams 1022$a$ and 1022$b$ are expelled from the output apertures 1020$a$ and 1020$b$ at respective angles relative to the longitudinal axis 1006. In some implementations, the capillaries 1020$a$ and 1020$b$ can be configured such that the streams 1022$a$ and 1022$b$ intersect at a point 1026 beyond the tip of the catheter 1002 (e.g., where the point 1026 is on or around the longitudinal axis 1006). For example, the streams 1022$a$ and 1022$b$ may mix without bubble formation or without significant bubble formation in the mixing region 1024 at a distance downstream from the output apertures of the capillaries 1018$a$ and 1018$b$.

Further, the communicating lumen 1010$a$ provides access to the vasculature of the patient. For example, in some implementations, a sensor module 1054 can be at least partially inserted into the communicating lumen 1010$a$, such that it is in fluid communication with the blood of the patient. In other implementations, the sensor may be located outside of the communicating lumen or on a catheter wall. The sensor(s) of the sensor module 1054 can obtain one or more sensor measurements regarding the blood and provide feedback regarding measured parameters affected by the $SSO_2$ therapy in order to optimize the $SSO_2$ therapy. For example, a sensor of the sensor module 1054 can measure a partial pressure of oxygen of the patient's blood, an oxygen concentration or $SO_2$ of the patient's blood, a pressure of the patient's blood, e.g., arterial blood pressure, a flow rate of the of the patient's blood, and/or a temperature of the of the patient's blood.

Examples of such sensors include the following:

One example of a sensor for measuring a partial pressure ($pO_2$) of oxygen or oxygen saturation $SO_2$ in the patient's blood is a pulse oximeter. A pulse oximeter may be used for estimating arterial $pO_2$ or $SO_2$. Pulse oximetry estimates the percentage of oxygen bound to hemoglobin in the blood. A pulse oximeter uses light-emitting diodes and a light-sensitive sensor to measure the absorption of red and infrared light. In another example, a sensor for measuring partial pressure of oxygen comprises an electrode such as a Clark electrode for measuring $pO_2$. A Clark electrode is an electrode that measures ambient oxygen concentration in a liquid using a catalytic platinum surface according to the net reaction $O_2$+4 e−+4 H+→2 $H_2O$. The various sensors may be coupled to a controller of the system via a cable or other wired connection or via a wireless connection.

The processor can receive the signals from these sensors, which signals correspond to the measured values of $pO_2$. The processor compares the measured $pO_2$ to a target range of blood $pO_2$, e.g., 760-1500 mmHg (about 100 kPa to 200 kPa). The target range may be calculated based on a blood flow rate of 50-1050 ml/min, saline flow rate of 2-5 ml/min and dissolved $O_2$ concentration in saline of 0.2-3 ml $O_2$/ml saline (STP). The controller can adjust the saline flow rate and/or dissolved $O_2$ concentration in saline based on the measured $pO_2$ in blood to achieve an arterial blood $pO_2$ within the target range. The processor may generate an alert, e.g., through a user interface, audible alarm and/or visual alarm that indicates the level of $pO_2$. The measured $pO_2$ indicates the effectiveness of the supersaturated oxygen therapy, letting the caregiver know if the $pO_2$ in blood is within the target range for optimizing the delivery of oxygen to the patient's ischemic tissue. In certain implementations, the processor may control the delivery of supersaturated oxygen therapy by modifying one or more of the above referenced saline or oxygen parameters based on the signals received from the sensors.

Another example of a sensor is an $O_2$ fluorescence probe. The fluorescence probe may be coupled to a controller of the system via a cable or other wired or wireless connection. A light source of the $O_2$ fluorescence probe is illuminated. A fiber optic cable can be used to provide light to the light source in certain implementations, where the fiber optic cable is connected to the controller of the system. The fluorescence of a sensor molecule of the $O_2$ fluorescence probe is measured. The sensor molecule can include fluorophore. A signal is received by the processor from the $O_2$ fluorescence probe based on the fluorescence measurement. Fluorescence is measured by measuring the lifetime or decay of the fluorescence intensity signal from the illuminated sensor molecule (e.g., fluorophore) on the fluorescence probe. The decay of this signal is caused by the quenching effect of oxygen molecules in the blood or in tissue on the fluorescence intensity signal of the sensor molecule. The processor can determine the oxygen concentration, $SO_2$ or $pO_2$ in blood or tissue based on the quenching effect of oxygen on the florescence intensity signal of the florescence probe. Changes in the amount of time that is required for the signal to decay due to oxygen quenching are indicative of the local oxygen concentration, $SO_2$ or $pO_2$ in blood or tissue. The processor generates an alert, e.g., through a user interface, audible alarm and/or visual alarm, based on the determined oxygen concentration, $SO_2$ or $pO_2$ in blood or tissue. The alert may indicate the effectiveness of the supersaturated oxygen therapy. The determined oxygen concentration, $SO_2$ or $pO_2$ indicates the effectiveness of the supersaturated oxygen therapy, letting the caregiver know if the oxygen concentration, $SO_2$ or $pO_2$ in blood is within a predefined target range (e.g., the expected range for a healthy individual) for optimizing the delivery of oxygen to the patient. In certain implementations, the processor may control the delivery of supersaturated oxygen therapy by modifying one or more of the saline or oxygen parameters, e.g., saline flow rate or dissolved $O_2$ concentration in saline, based on the determined oxygen concentration, $SO_2$ or $pO_2$ values.

Another example of a sensor is a temperature sensor located on or in the catheter. For example, a thermistor may be utilized to measure the blood temperature of the patient. The processor can receive signals from the thermistor, which signals correspond to the measured values of the blood temperature. The processor may generate an alert, e.g., through a user interface, audible alarm and/or visual alarm that indicates the blood temperature, which may alert the caregiver of a hypothermic or hyperthermic, e.g., febrile, state of the patient.

An example sensor for measuring an arterial pressure of the patient's blood would be a pressure sensor positioned in or coupled to the communicating lumen. The communicating lumen may be used for direct measurement of arterial pressure. The communicating lumen may be connected to a fluid-filled system, which is connected to an electronic pressure transducer. A change in detected blood pressure may be indicative of improved perfusion and/or restored flow in ischemic tissue as a result of the $SSO_2$ therapy. The therapy may result in improved heart function. In certain implementations, the processor may control the delivery of supersaturated oxygen therapy based on the arterial pressure feedback.

An example sensor 134, 334 used to determine a blood flow rate includes a temperature sensor, e.g., a thermistor, thermocouple or thermal anemometer. A temperature sensor may be located on a catheter tip, capillary tip or in the communication lumen. The temperature sensor may be heated, such that the sensor temperature is raised. As blood flows past the temperature sensor, the degree to which the temperature sensor cools down is indicative of the flow rate past the temperature sensor. The determined blood flow rate may be fed back to the system and may be indicative of the efficacy of the $SSO_2$ therapy, which results in improved perfusion and/or restored flow in ischemic tissue. In certain implementations, the processor may control the delivery of supersaturated oxygen therapy based on the blood flow rate feedback.

If the sensor is a pressure sensor, the sensor may detect a pressure differential between ambient pressure and arterial pressure or an absolute value of arterial pressure. The pressure sensor may be placed anywhere in the communicating lumen but does not necessarily have to be positioned in the communicating lumen, and can be located outside of the lumen. One example of a pressure sensor is a strain gauge. In a catheter having multiple communicating lumens, a pressure sensor may be located in a first communicating lumen providing an uninterrupted pressure signal while blood sampling may be performed via a second communicating lumen simultaneously. In another example, two pressure sensors can be used, with one located in a first communicating lumen and one located in a second communicating lumen to provide redundancy of pressure readings.

As another example, in some implementations, a sample extraction device 1056 can be used to obtain a sample of the patient's blood via the communicating lumen 1010*a*. For example, the sample extraction device 1056 can include one or more pumps or syringes to draw a sample of the patient's blood through the lumen 1010*a* and out of the patient's body. The syringe may be coupled to a proximal end of the catheter for sampling. A valve or stopcock may be included at the proximal end of one more lumen of the catheter to control sampling.

In some implementation, the communicating lumen 1010*a* can also be used to guide the catheter 1002 within the patient's body. For example, a guide wire can be inserted into the communicating lumen 1010*a*, and manipulated to control the shape and/or position of the catheter 1002 within the patient's body.

Further, the catheter 1002 may be configured in such a way that eliminates or otherwise reduces the formation of bubbles within the vasculature of the patient. For example, the streams 1022*a* and 1022*b* mix in a mixing region 1024 away from any surfaces of the catheter 1002 or capillaries thereby reducing, preventing or reducing the likelihood of bubble formation through nucleation on the surfaces of the catheter 1002 or capillaries. In some implementations, the catheter 1002 can also include one or more shields or guards 1028 (e.g., protrusions, walls, bumps, etc.) positioned over the output aperture 1012*b* to reduce nucleation along one or more surfaces of the catheter.

Figure 11:
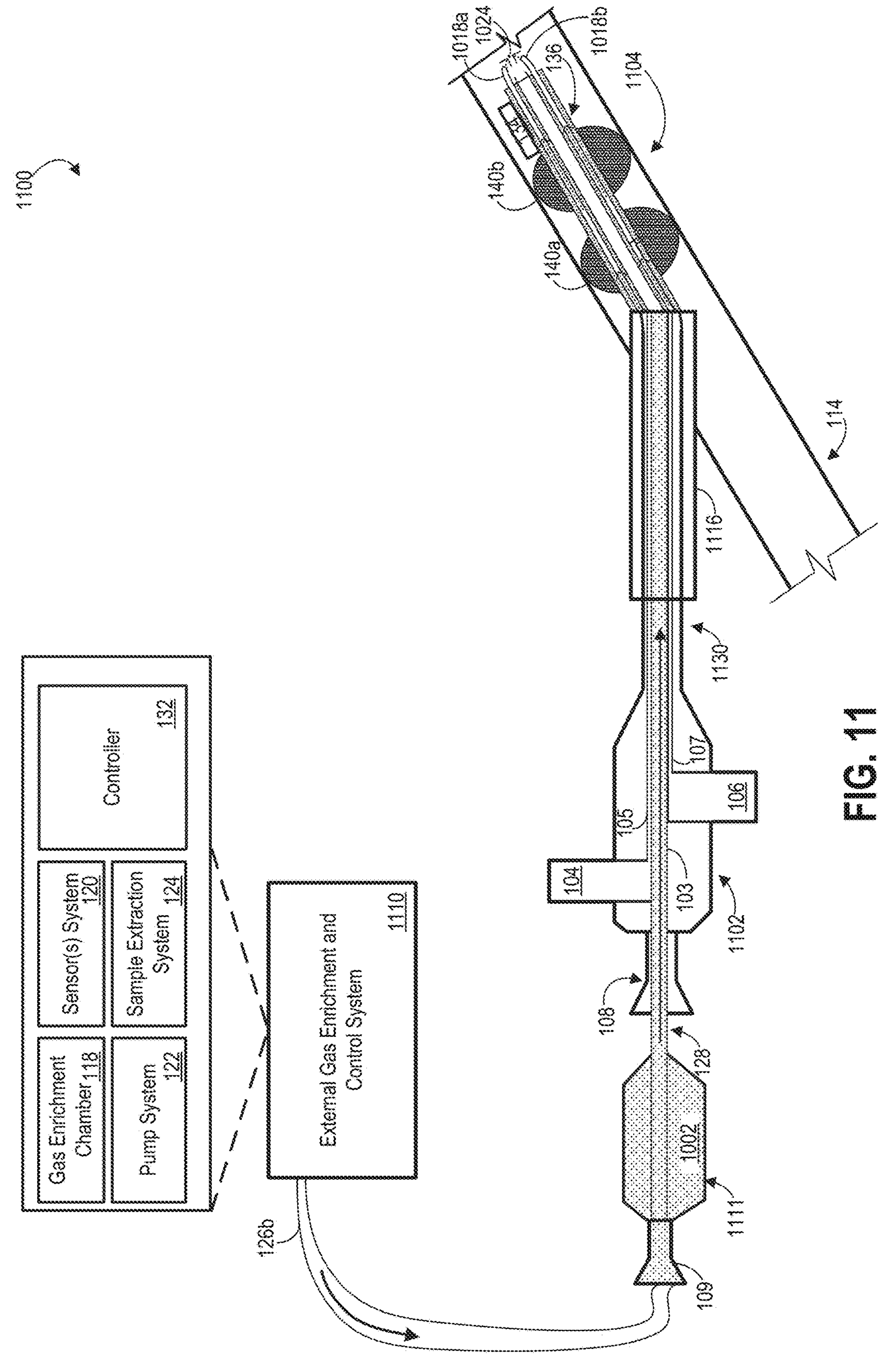
FIG. 11 is a diagram of an example system for delivering gas-enriched liquid within the vasculature of a patient.

FIG. 11 is a diagram of an example system 1100 for delivering gas-enriched liquid within the vasculature of a patient. The system 1100 is configured for direct injection of gas-enriched fluid by a first catheter 1002 (as shown in FIG. 10). The system 1100 is similar to system 100 described in relation to FIG. 1. Rather than using a circuit in which blood is drawn from a patient, mixed with a gas-enriched liquid and the resulting gas-enriched blood is returned to the patient, the gas enrichment and control system 1110 is configured to enrich a liquid (e.g., saline) with oxygen, e.g., in an atomization chamber in the gas-enrichment chamber 118, and deliver, via catheter 1002, at mixing point 1024, the gas-enriched liquid to the vasculature 114 of the patient directly.

The system 1100 includes a first catheter 1002 that is configured to perform direct injection of gas-enriched liquid, e.g., $SSO_2$ liquid, and a second catheter 1130 which is configured to perform partial (or total) occlusion of the vasculature 114 of the patient. As previously described, balloons 140*a-b* can inflate for partial occlusion of the vasculature. Catheter 1002 includes capillaries 1018*a-b* for generating the streams 1020*a-b* as previously described. The catheter 1002 is connected to a $SSO_2$ catheter hub 1111 that is similar to $SSO_2$ catheter hub 1111.

The second catheter or occlusion catheter 1130 is similar to occlusion catheter 130, and includes balloons 140*a-b* for partial or total occlusion as previously described. The occlusion catheter 1130 includes an occlusion catheter hub 1102, which is similar to occlusion catheter hub 102. The $SSO_2$ catheter 1002 can be inserted through occlusion catheter hub 1102 in a similar manner as described in relation to FIG. 1. Both the $SSO_2$ catheter 1002 and the occlusion catheter 1130 may optionally be inserted into the vasculature 114 through a sheath 1116. Generally, the sheath 1116 is similar to sheath 116, except sheath 1116 does not include a return port for extracting blood from the vasculature 114. The $SSO_2$ catheter 1002 can be inserted through the occlusion catheter 1130 so that the $SSO_2$ catheter 1002 can deliver gas enriched liquid through capillaries 1018*a-b* while the occlusion balloons 140*a-b* of the occlusion catheter 1130 partially obstruct a flow of blood within the vasculature of the patient, and divert the blood flow to the region where the gas-enriched liquid is delivered.

In some implementations, the occlusion structure 140*a-b* partially obstructs the flow of blood within the vasculature by producing a vessel occlusion of 20-80%. In some implementations, the occlusion structure partially obstructs the flow of blood such that the blood flow rate is 20-80% of a non-occluded blood flow rate. In some implementations, the process 1100 includes receiving, from one or more sensors 134, a signal representing a measured blood pressure in the vasculature of the patient. In some implementations, the process 1100 includes, based on the measured blood pressure, adjusting an occlusion percentage in the vasculature of the patient caused by an occlusion structure 140*a-b* of the catheter.

In some implementations, the controller 132 is configured for receiving, from one or more sensors, a signal representing a measured $pO_2$ in the vasculature of the patient. In some implementations, the controller 132 is configured to, based on the measured $pO_2$, adjust a concentration of oxygen in the gas-enriched liquid. In some implementations, the controller 132 is configured for delivering the gas-enriched liquid having the adjusted concentration of oxygen to the region of the vasculature of the patient.

In some implementations, the controller 132 is configured for adjusting both the concentration of gas in a gas-enriched liquid and the occlusion percentage in the vasculature of the patient.

In some implementations, the gas-enriched liquid comprises a supersaturated oxygen liquid. In some implementations, the supersaturated oxygen liquid has an $O_2$ concentration of 0.1-6 ml $O_2$/ml liquid (STP). In some implementations, the gas-enriched liquid comprises a supersaturated oxygen enriched liquid.

Figure 12:
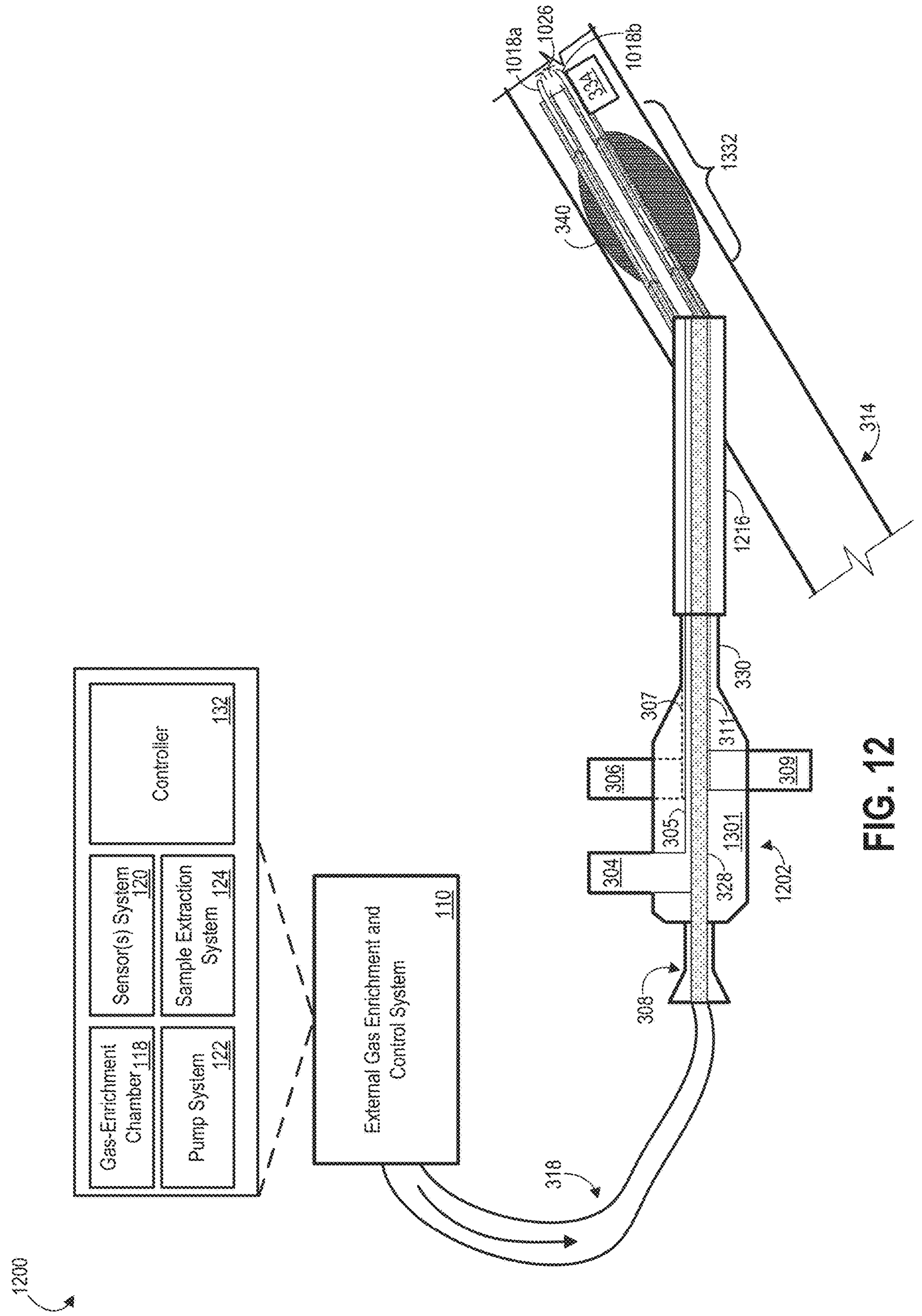
FIG. 12 is a diagram of an example system for delivering gas-enriched liquid within the vasculature of a patient.

FIG. 12 is a diagram of an example system 1200 for delivering gas-enriched liquid within the vasculature of a patient. The system 1200 includes an integrated catheter 1202 for performing both occlusion and $SSO_2$ delivery, similar to integrated catheter 302 of FIG. 3. The integrated catheter 1202 is configured for direct injection of gas-enriched liquid though capillaries 1018*a-b* at mixing point 1026 within the vasculature 314 while the occlusion balloon 340 partially obstructs a flow of blood within the vasculature of the patient, and diverts the blood flow to the region where the gas-enriched liquid is delivered.

Similar to portion 332 of FIG. 3, the occlusion portion 1332 of the integrated catheter 1202 includes at least one balloon 340 for partial or total occlusion of the vasculature 314. There is no return port for drawing blood from the patient in either sheath 1216 (which may be optional) or integrated catheter hub 1301. The integrated catheter 1202 is configured for both occlusion, and for delivery of gas-enriched liquid as described for catheter 1002 in relation to FIG. 10.

In some implementations, the occlusion structure 1332 partially obstructs the flow of blood within the vasculature by producing a vessel occlusion of 20-80%. In some implementations, the occlusion structure 1332 partially obstructs the flow of blood such that the blood flow rate is 20-80% of a non-occluded blood flow rate. In some implementations, the controller 132 receives, from one or more sensors 334, a signal representing a measured blood pressure in the vasculature of the patient. The controller 132 is configured, based on the measured blood pressure, for adjusting an occlusion percentage in the vasculature of the patient caused by an occlusion structure of the catheter. In some implementations, the controller 132 is configured for receiving, from one or more sensors, a signal representing a measured $pO_2$ in the vasculature of the patient. In some implementations, the controller 132 is configured for, based on the measured $pO_2$, adjusting a concentration of oxygen in the gas-enriched liquid. In some implementations, the controller 132 is configured for delivering the gas-enriched liquid having the adjusted concentration of oxygen to the region of the vasculature of the patient.

In some implementations, the controller 132 is configured for adjusting both the concentration of gas in a gas-enriched liquid and the occlusion percentage in the vasculature of the patient. In some implementations, the gas-enriched liquid comprises a supersaturated oxygen liquid. In some implementations, the supersaturated oxygen liquid has an $O_2$ concentration of 0.1-6 ml $O_2$/ml liquid (STP). In some implementations, the gas-enriched liquid comprises a supersaturated oxygen enriched liquid.

Figure 13:
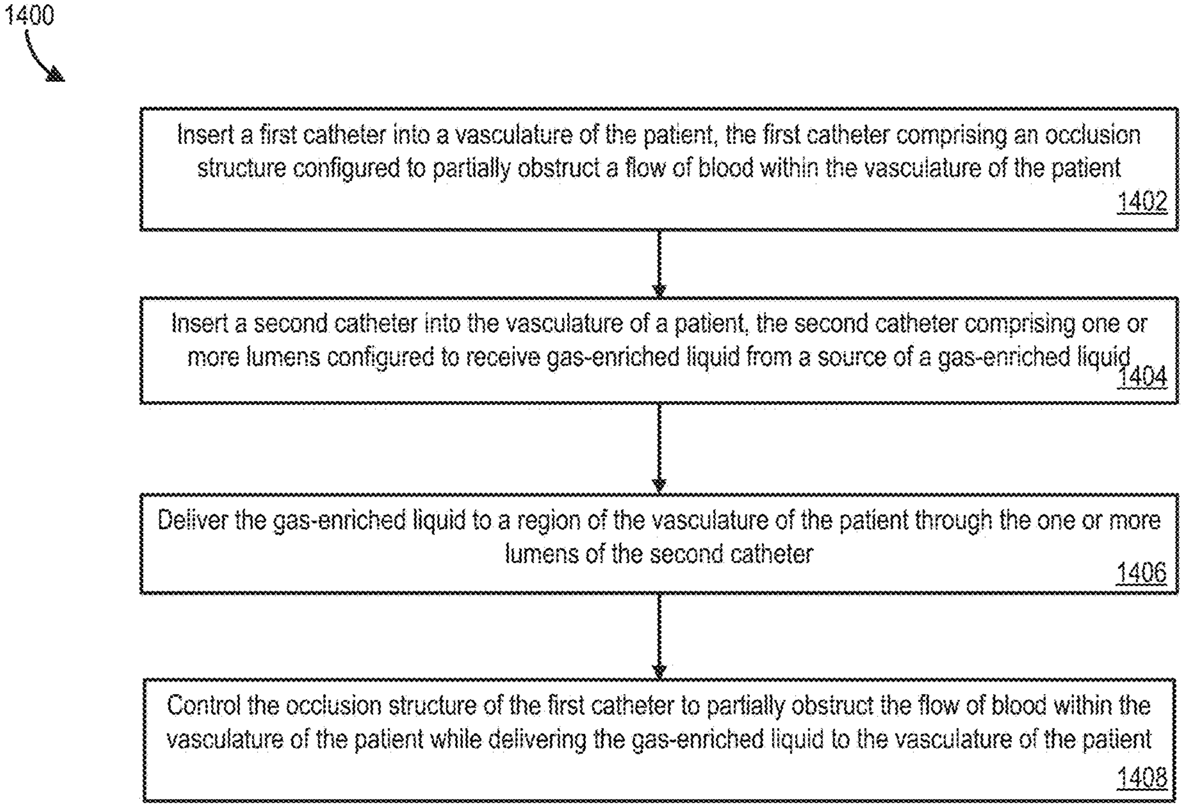
FIG. 13 shows a flow diagram including an example process for providing combined gas enrichment and partial occlusion therapy.

FIG. 13 shows a flow diagram including an example process 1400 for providing combined gas enrichment and partial occlusion therapy. Process 1400 can be associated with the catheters described previously such as in relation to FIGS. 10-11. Process 1400 includes inserting (1402) a first catheter into a vasculature of the patient, the first catheter comprising an occlusion structure configured to partially obstruct a flow of blood within the vasculature of the patient. Process 1400 includes inserting (1404) a second catheter into the vasculature of a patient, the second catheter comprising one or more lumens configured to receive gas-enriched liquid from a source of a gas-enriched liquid. Process 1400 includes delivering (1406) the gas-enriched liquid to a region of the vasculature of the patient through the one or more lumens of the second catheter. Process 1400 includes controlling (1408) the occlusion structure of the first catheter to partially obstruct the flow of blood within the vasculature of the patient. In some implementations, the first catheter partially obstructs the flow of blood within the vasculature of the patient while allowing the second catheter to deliver the gas-enriched liquid to the region of the vasculature of the patient, and diverts the blood flow to the region where the gas-enriched liquid is delivered. In some implementations, the second catheter comprises two or more capillaries extending from a tip of the second catheter, the two or more capillaries each configured to deliver a stream of the gas-enriched liquid to the vasculature of the patient. In some implementations, the stream of the gas-enriched liquid (e.g., $SSO_2$) from each capillary of the two or more capillaries is configured to mix with other streams from the other capillaries of the two or more capillaries inside the vasculature of the patient.

In some implementations, the first catheter comprises two or more capillaries extending from a tip of the first catheter, the two or more capillaries configured to simultaneously dispense respective streams of the gas enriched liquid directly into the vasculature of the patient. In some implementations, the first catheter is configured to position the two or more capillaries at one or more predetermined angles relative to one another, such that the streams of the gas enriched liquid intersect and mix with the patient's blood. In some implementations, one or more sensors are coupled to the first and/or second catheter. The one or more sensors are configured to measure one or more parameters of blood of the patient. Operation of the first catheter, the second catheter, or both the first catheter and the second catheter are controlled based on the measured one or more parameters. In some implementations, the process 1400 includes receiving, from one or more sensors, a signal representing a measured blood pressure in the vasculature of the patient. In some implementations, the process 1400 includes, based on the measured blood pressure, adjusting an occlusion percentage in the vasculature of the patient caused by an occlusion structure of the catheter.

In some implementations, the process 1400 includes receiving, from one or more sensors, a signal representing a measured $pO_2$ in the vasculature of the patient. In some implementations, the process 1400 includes, based on the measured $pO_2$, adjusting a concentration of oxygen in the gas-enriched liquid. In some implementations, the process 1400 includes delivering the gas-enriched liquid having the adjusted concentration of oxygen to the region of the vasculature of the patient. In some implementations, the process 1400 includes adjusting both the concentration of gas in a gas-enriched liquid and the occlusion percentage in the vasculature of the patient. In some implementations, the gas-enriched liquid comprises a supersaturated oxygen liquid.

In some implementations, the supersaturated oxygen liquid has an $O_2$ concentration of 0.1-6 ml $O_2$/ml liquid (STP).

Figure 14:
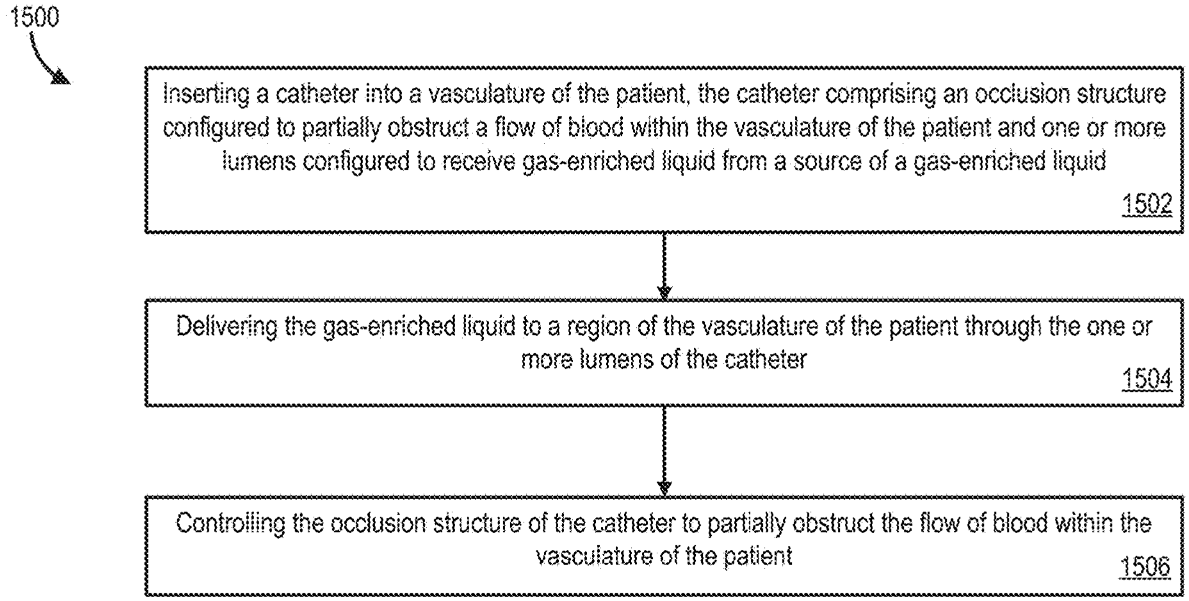
FIG. 14 shows a flow diagram including an example process for providing combined gas enrichment and partial occlusion therapy.

FIG. 14 shows a flow diagram including an example process 1500 for providing combined gas enrichment and partial occlusion therapy. Process 1500 can be associated with the catheters described previously such as in relation to FIGS. 10 and 12. Process 1500 includes inserting (1502) a catheter into a vasculature of the patient, the catheter comprising an occlusion structure configured to partially obstruct a flow of blood within the vasculature of the patient and one or more lumens configured to receive gas-enriched liquid from a source of a gas-enriched liquid. Process 1500 includes delivering (1504) the gas-enriched liquid to a region of the vasculature of the patient through the one or more lumens of the catheter. Process 1500 includes controlling (1506) the occlusion structure of the catheter to partially obstruct the flow of blood within the vasculature of the patient. In some implementations, the catheter partially obstructs the flow of blood within the vasculature of the patient while delivering the gas-enriched liquid (e.g., $SSO_2$) to the region of the vasculature of the patient, and diverts the blood flow to the region where the gas-enriched liquid is delivered. In some implementations, the second catheter comprises two or more capillaries extending from a tip of the second catheter, the two or more capillaries each configured to deliver a stream of the gas-enriched liquid to the vasculature of the patient. In some implementations, the stream of the gas-enriched liquid from each capillary of the two or more capillaries is configured to mix with other streams from the other capillaries of the two or more capillaries inside the vasculature of the patient.

In some implementations, the first catheter comprises two or more capillaries extending from a tip of the first catheter, the two or more capillaries configured to simultaneously dispense respective streams of the gas enriched liquid directly into the vasculature of the patient. In some implementations, the first catheter is configured to position the two or more capillaries at one or more predetermined angles relative to one another, such that the streams of the gas enriched liquid intersect and mix with the patient's blood. In some implementations, one or more sensors are coupled to the first and/or second catheter. The one or more sensors are configured to measure one or more parameters of blood of the patient. Operation of the first catheter, the second catheter, or both the first catheter and the second catheter are controlled based on the measured one or more parameters. In some implementations, the process 1500 includes receiving, from one or more sensors, a signal representing a measured blood pressure in the vasculature of the patient. In some implementations, the process 1500 includes, based on the measured blood pressure, adjusting an occlusion percentage in the vasculature of the patient caused by an occlusion structure of the catheter.

In some implementations, the process 1500 includes receiving, from one or more sensors, a signal representing a measured $pO_2$ in the vasculature of the patient. In some implementations, the process 1500 includes, based on the measured $pO_2$, adjusting a concentration of oxygen in the gas-enriched liquid. In some implementations, the process 1500 includes delivering the gas-enriched liquid having the adjusted concentration of oxygen to the region of the vasculature of the patient. In some implementations, the process 1500 includes adjusting both the concentration of gas in a gas-enriched liquid and the occlusion percentage in the vasculature of the patient. In some implementations, the gas-enriched liquid comprises a supersaturated oxygen liquid.

In some implementations, the supersaturated oxygen liquid has an $O_2$ concentration of 0.1-6 ml $O_2$/ml liquid (STP).

While several of the above examples refer to partial obstruction of the flow of blood within the vasculature by producing a partial vessel occlusion or partial occlusion in the vasculature using one or more occlusion structures, while allowing for the delivery of gas-enriched blood or supersaturated oxygen enriched liquid to the vasculature, alternatively, in certain implementations, the vessel occlusion may be a full occlusion, which may result in a full obstruction of the flow of blood through the occluded vessel, while allowing for the delivery of gas-enriched blood or supersaturated oxygen enriched liquid to the vasculature.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, various modifications can be made without departing from the scope of the disclosure. Accordingly, other embodiments are within the scope of the claims.

What is claimed is:

1. A system for delivering gas-enriched liquid within a vasculature of a patient while partially obstructing a flow of blood within the vasculature of the patient, the system comprising:

a source of a gas-enriched liquid;

a first catheter coupled to the source of the gas-enriched liquid, the first catheter configured to be inserted into a vasculature of a patient and deliver the gas-enriched liquid to a region of the vasculature of the patient, the first catheter comprising one or more lumens configured to receive the gas-enriched liquid from the source of the gas-enriched liquid;

a second catheter configured to be inserted into the vasculature of the patient through the first catheter, the second catheter comprising one or more lumens and an occlusion structure configured to partially obstruct the flow of blood within the vasculature of the patient while allowing the first catheter to deliver the gas-enriched liquid to the region of the vasculature, the occlusion structure of the second catheter configured to divert the flow of blood to the region where the gas-enriched liquid is delivered by the first catheter; and a controller and one or more sensors, wherein the one or more sensors are configured to measure one or more parameters of the blood within the vasculature of the patient, wherein the controller is configured to control, based on the measured one or more parameters, oxygen delivery and the occlusion structure to divert the flow of the blood to the region where the gas-enriched liquid is delivered by the first catheter.

2. The system of claim 1, wherein the first catheter comprises two or more capillaries extending from a tip of the first catheter, the two or more capillaries configured to simultaneously dispense respective streams of the gas-enriched liquid directly into the vasculature of the patient.

3. The system of claim 2, wherein the first catheter is configured to position the two or more capillaries at one or more predetermined angles relative to one another, such that the streams of the gas-enriched liquid intersect and mix with blood of the patient.

4. The system of claim 1, wherein the controller is configured for receiving, from one or more sensors, a signal representing a measured blood pressure in the vasculature of the patient and based on the measured blood pressure, adjusting an occlusion percentage in the vasculature of the patient caused by the occlusion structure of the second catheter.

5. The system of claim 1, wherein the controller is configured for:

receiving, from the one or more sensors, a signal representing a measured $pO_2$ in the vasculature of the patient;

based on the measured $pO_2$, adjusting a concentration of oxygen in the gas-enriched liquid; and delivering the gas-enriched liquid having the adjusted concentration of oxygen to the region of the vasculature of the patient.

6. The system of claim 1, wherein the controller is configured for:

adjusting both a concentration of gas in a gas-enriched liquid and an occlusion percentage in the vasculature of the patient.

7. The system of claim 1, wherein the source of the gas-enriched liquid comprises a gas-enrichment chamber configured to form the gas-enriched liquid by mixing gas with atomized liquid.

8. The system of claim 1, wherein the gas-enriched liquid comprises a supersaturated oxygen liquid.

9. The system of claim 8, wherein the supersaturated oxygen liquid has an O2 concentration of 0.1-6 ml O2/ml liquid (STP).

10. The system of claim 1, wherein the occlusion structure is configured to partially obstruct the vasculature of the patient within a target occlusion percentage and to control the flow of blood within the vasculature of the patient while allowing the first catheter to deliver the gas-enriched liquid to the region of the vasculature, the occlusion structure of the second catheter configured to divert the flow of blood to the region where the gas-enriched liquid is delivered by the first catheter.

11. The system of claim 1, wherein the controller is configured to control the occlusion structure by oscillating a size of the occlusion structures to prevent cytokine buildup at or near the occlusion structure.

12. The system of claim 1, wherein the controller is configured to increase a size of the occlusion structure in an initial control phase and gradually reducing the size of the occlusion structure in a subsequent control phase until a blood pressure is within a target range and increase a concentration of oxygen in the initial control phase and gradually reduce the concentration of oxygen in the subsequent control phase until an oxygen level within a target range.

13. The system of claim 12, wherein the target range of the oxygen level is between 60-80% or 65-75% cerebral oxygen saturation.

14. The system of claim 1, wherein a diameter of the occlusion structure is between about 5-30 millimeters to partially obstruct the flow of blood within the vasculature of the patient while allowing the first catheter to deliver the gas-enriched liquid to the region of the vasculature.

15. The system of claim 1, wherein a diameter of the occlusion structure is between about 9-26 millimeters to partially obstruct the flow of blood within the vasculature of the patient while allowing the first catheter to deliver the gas-enriched liquid to the region of the vasculature.

16. The system of claim 1, wherein a volume of the occlusion structure is between about 3-60 milliliters to partially obstruct the flow of blood within the vasculature of the patient while allowing the first catheter to deliver the gas-enriched liquid to the region of the vasculature.

17. The system of claim 1, wherein the second catheter and the occlusion structure have an outside diameter of about 0.050 to 0.200 inches to partially obstruct the flow of blood within the vasculature of the patient while allowing the first catheter to deliver the gas-enriched liquid to the region of the vasculature.

18. The system of claim 1, wherein the occlusion structure is controlled to within a range of 30-70% of partial vessel occlusion to partially obstruct the flow of blood within the vasculature of the patient while allowing the first catheter to deliver the gas-enriched liquid to the region of the vasculature.

19. The system of claim 1, wherein the occlusion structure is controlled to within a range of 40-60% of partial vessel occlusion to partially obstruct the flow of blood within the vasculature of the patient while allowing the first catheter to deliver the gas-enriched liquid to the region of the vasculature.

* * * * *